United States Patent
Tymianski et al.

(10) Patent No.: US 9,610,323 B2
(45) Date of Patent: *Apr. 4, 2017

(54) MODEL SYSTEMS AND TREATMENT REGIMES FOR TREATMENT OF NEUROLOGICAL DISEASE

(71) Applicant: NoNO Inc., Toronto (CA)

(72) Inventors: Michael Tymianski, Toronto (CA); Jonathan David Garman, Thornhill (CA)

(73) Assignee: NoNO INC., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/597,166

(22) Filed: Jan. 14, 2015

(65) Prior Publication Data
US 2015/0202253 A1    Jul. 23, 2015

Related U.S. Application Data

(63) Continuation of application No. 13/377,523, filed as application No. PCT/US2010/038200 on Jun. 10, 2010, now Pat. No. 8,940,699.

(60) Provisional application No. 61/185,989, filed on Jun. 10, 2009.

(51) Int. Cl.
*A61K 38/00* (2006.01)
*A61K 45/06* (2006.01)
*A61K 38/16* (2006.01)

(52) U.S. Cl.
CPC ............ *A61K 38/162* (2013.01); *A61K 45/06* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 8,940,699 B2 | 1/2015 | Tymianski et al. | |
| 2002/0098179 A1 | 7/2002 | Brearley et al. | |
| 2005/0059597 A1 | 3/2005 | Tymianski | |
| 2012/0208764 A1 | 8/2012 | Tymianski | |
| 2013/0156704 A1 | 6/2013 | Tymianski | |
| 2014/0248257 A1 | 9/2014 | Tymianski et al. | |

FOREIGN PATENT DOCUMENTS

| | | | |
|---|---|---|---|
| CA | 2524573 A1 | 11/2004 | |
| WO | WO 2008/008348 A2 | 1/2008 | |
| WO | WO 2008/014917 A1 | 2/2008 | |
| WO | WO 2008/109010 A1 | 9/2008 | |
| WO | WO 2010/144721 A2 | 12/2010 | |
| WO | WO 2012/176172 A2 | 12/2012 | |
| WO | WO 2013/088382 A1 | 6/2013 | |

OTHER PUBLICATIONS

EPO Application No. 12857611.3, Supplementary European Search Report and European Search Opinion mailed Aug. 21, 2015.
Grasso et al., "An overview of new pharmacological treatments for cerebrovascular dysfunction after experimental subarachnoid hemorrhage," Brain Research Reviews, 44(1):49-63, (2004).
Lantos et al., "CT perfusion for stroke: should you use it?" Physicians Practice, 6 pages, (2010). [Retrieved from the Internet Oct. 28, 2015: <URL: http://www.physicianspractice.com/ct/ct-perfusion-stroke-should-you-use-it/page/0/2 >].
Saver, "Intra-arterial thrombolysis," Neurology, 57(Suppl 2):S58-S60, (2001).
U.S. Appl. No. 13/774,053, Notice of Allowance mailed Sep. 3, 2015.
U.S. Appl. No. 14/128,941, Non-Final Office Action mailed Nov. 4, 2015.
U.S. Appl. No. 14/128,941, Requirement for Restriction/Election mailed Jun. 5, 2015.
"Abstracts of the 46th Annual Congress of the Canadian Neurological Sciences Federation," Can J Neurol Sci, 38(3):1-94, (2011).
"Novel Therapeutic Compounds for Subarachnoid Hemorrhage," Cognosci, Inc., 3 pages, (2007). [Retrieved from the Internet May 13, 2014: <URL: http://www.cognosci.com/documents/sah__white_paper.pdf>].
"Species Dosage Conversion Factors," National Cancer Institute (NCI), Frederick National Laboratory for Cancer Research, Laboratory Animal Sciences Program (LASP), Animal Care and Use Committee (ACUC) Guidelines, ACUC 42.00, 1 page, (2007). [Retrieved from the Internet Jul. 15, 2014: <URL: https://ncifrederick.cancer.gov/Lasp/Acuc/Frederick/Media/Documents/ACUC42.pdf>].
"Subarachnoid Hemorrhage," The Free Online Medical Dictionary, 7 pages, (2001). [Retrieved from the Internet Aug. 6, 2013: <URL: http://medical-dictionary.thefreedictionary.com/subarachnoid+hemorrhage>].
Aarts et al., "Treatment of Ischemic Brain Damage by Perturbing NMDA Receptor-PSD-95 Protein Interactions," Science, 298(5594):846-850, (2002).
Ardizzone et al., "SRC kinase inhibition improves acute outcomes after experimental intracerebral hemorrhage," Stroke, 38:1621-1625, (2007).
Bang et al., "Specific DWI lesion patterns predict prognosis after acute ischaemic stroke within the MCA territory," J Neurol Neurosurg Psychiatry, 76:1222-1228, (2005).
Bratane et al., "Neuroprotection by freezing ischemic penumbra evolution without cerebral blood flow augmentation with a post-synaptic density-95 protein inhibitor," Stroke, 42(11):3265-3270, (2011).
Brooks et al., "Frequency of thromboembolic events associated with endovascular aneurysm treatment: retrospective case series", Journal of Neurosurg, 108:1095-1100, (2008).
ClinicalTrials.gov Identifier NCT00728182, "Evaluating Neuroprotection in Aneurysm Coiling Therapy (ENACT)," ClinicalTrials.gov, Full Text View, U.S. National Institutes of Health, Aug. 1, 2008.
Cook et al., "Treatment of stroke with a PSD-95 inhibitor in the gyrencephalic primate brain," Nature, 483(7388):213-217, (2012).

(Continued)

Primary Examiner — Adam M Weidner
(74) Attorney, Agent, or Firm — Alston & Bird LLP

(57) ABSTRACT

The invention provides animal models and clinical trials for assessing agents for potential use in treating and effecting prophylaxis stroke and other neurological diseases, particularly those mediated at least in part by excitoxity. The invention also provides preferred dosage and infusion regimes and pharmaceutical compositions for clinical application of such agents.

12 Claims, 5 Drawing Sheets

(56) References Cited

OTHER PUBLICATIONS

Cronqvist et al., "Diffusion and perfusion MRI in patients with ruptured and unruptured intracranial aneurysms treated by endovascular coiling: complications, procedural results, MR findings and clinical outcome," Neuroradiology, 47:855-873, (2005).
Cui et al. "PDZ protein interactions underlying NMDA receptor-mediated excitotoxicity and neuroprotection by PSD-95 inhibitors," J. Neurosci., 27(37):9901-9915, (2007).
Davis et al., "Termination of Acute Stroke Studies Involving Selfotel Treatment," The Lancet, 349:32-32, (1997).
Donnan et al., "How to make better use of thrombolytic therapy in acute ischemic stroke," Nat Rev Neurol., 7(7): 400-409, (2011).
EPO Application No. 10786859.8, Supplementary European Search Report and European Search Opinion mailed Apr. 30, 2014.
EPO Application No. EP 12802409.8, Supplementary European Search Report and European Search Opinion mailed Nov. 12, 2014.
Fan et al., "N-Methyl-D-aspartate receptor subunit- and neuronal-type dependence of excitotoxic signaling through post-synaptic density 95," Journal of Neurochemistry, 115(4):1045-1056, (2010).
Fan, et al. "Interaction of postsynaptic density protein-95 with NMDA receptors influences excitotoxicity in the yeast artificial chromosome mouse model of Huntington's disease," J. Neurosci., 29(35):10928-10938, (2009).
Florio, et al. "Disruption of nNOS-PSD95 Protein-protein Interaction Inhibits Acute Thermal Hyperalgesia and Chronic Mechanical Allodynia in Rodents", Brit. J. Pharmacol., 158(2):494-506, (2009).
Germano et al., "NMDA receptor antagonist felbamate reduces behavioral deficits and blood-brain barrier permeability changes after experimental subarachnoid hemorrhage in the rat," J Neurotrauma, 24(4):732-744, (2007).
Haley et al., "A randomized, double-blind, vehicle-controlled trial of tirilazad mesylate in patients with aneurysmal subarachnoid hemorrhage: a cooperative study in North America," J Neurosurg, 86(3):467-474, (1997). Abstract Only.
Herce, et al., "Molecular dynamics simulations suggest a mechanism for translocation of the HIV-1 TAT peptide across lipid membranes," Proc. Natl. Acad. Sci. U. S. A., 104(52):20805-20810, (2007).
Hill et al., "Safety and efficacy of NA-1 in patients with iatrogenic stroke after endovascular aneurysm repair (ENACT): a phase 2, randomised, double-blind, placebo-controlled trial," The Lancet Neurology, 11(11):942-950, (2012).
Horn et al., "Very Early Nimodipine Use in Stroke (VENUS): A Randomized, Double-Blind, Placebo-Controlled Trial," Stroke, 32:461-465, (2001).
Kaufmann et al., "Complications of Diagnostic Cerebral Angiography: Evaluation of 19 826 Consecutive Patients", Radiology, 243(3):812-819, (2007).
Kleckner et al., "Subtype-Selective Antagonism of N-Methyl-o-Aspartate Receptors by Felbamate: Insights into the Mechanism of Action," JPET, 289(2):898-894, (1999).
Kusaka et al., "Signaling pathways for early brain injury after subarachnoid hemorrhage," J Cerebral Blood Flow & Metabolism, 24:916-925, (2004).
Lanzino et al., "Double-blind, randomized, vehicle-controlled study of high-dose tirilazad mesylate in women with aneurysmal subarachnoid hemorrhage. Part II. A cooperative study in North America," J Neurosurg, 90(6):1018-1024 , (1999). Abstract Only.
Lees, "Cerestat and other NMDA antagonists in ischemic stroke," Neurology, 49(Suppl 4):S66-S69, (1997).
Li, "Pharmacologically Induced Histamine Release: Sorting Out Hypersensitivity Reactions to Opioids," Publication, 35(4):1,14-16, (2006).
Martel, et al., "Inhibiting pro-death NMDA receptor signaling dependent on the NR2 PDZ ligand may not affect synaptic function or synaptic NMDA receptor signaling to gene expression," Channels (Austin), 3(1):12-15, (2009).
Miyazawa et al., "Effect of mild hypothermia on focal cerebral ischemia. Review of experimental studies," Neurol Res, 25(5):457-464, (2003). Abstract Only.

Morgan et al., "Chapter 9: Neuromuscular Blocking Agents," Clinical Anesthesiology, 4th Edition, McGraw-Hill Companies, Inc., 32 pages, (2006). [Retrieved from the Internet Jan. 7, 2014: <URL: http://bentollenaar.com/MM_Book/Ch.9.htm>].
Nelson et al., "Myristoyl-based transport of peptides into living cells," Biochem, 46(51):14771-14781, (2007).
Sam "Differential protein interactions of nmda receptor NR2 subunits" Doctoral thesis; University of Toronto,. (2010).
Sena et al., "Systematic Review and Meta-Analysis of the Efficacy of Tirilazad in Experimental Stroke," Publication,Stroke, 38:388-394, (2007). Retrieved from the Internet Dec. 3, 2014: <URL: http://stroke.ahajournals.org/content/38/2/388/>].
Soriano, et al., "Specific targeting of pro-death NMDA receptor signals with differing reliance on the NR2B PDZ ligand," J. Neurosci., 28(42):10696-1071015, (2008).
Sturgill et al., "Distinct domains within psd-95 mediate synaptic incorporation, stabilization, and activity-dependent trafficking," J neurosci, 29(41):12845-12854, (2009).
Sun, et al. "Effectiveness of PSD95 inhibitors in permanent and transient focal ischemia in the rat," Stroke, 39(9):2544-2553, (2008).
Todd et al., "Mild Intraoperative Hypothermia during Surgery for Intracranial Aneurysm," N Engl J Med, 352:135-145, (2005).
U.S. Appl. No. 13/377,523, Final Office Action mailed Jan. 15, 2014.
U.S. Appl. No. 13/377,523, Non-Final Office Action mailed Apr. 29, 2013.
U.S. Appl. No. 13/377,523, Notice of Allowance and Examiner Initiated Interview Summary mailed Sep. 12, 2014.
U.S. Appl. No. 13/774,053, Final Office Action mailed Jan. 15, 2014.
U.S. Appl. No. 13/774,053, Non-Final Office Action and Examiner Initiated Interview Summary mailed Jun. 3, 2014.
U.S. Appl. No. 13/774,053, Non-Final Office Action mailed Aug. 14, 2013.
Westermaier, "Neuroprotective Treatment Strategies for Delayed Cerebral Ischemia after Subarachnoid Hemorrhage—Review of Literature and Future Prospects," J Neural Neurophysiol, 5(1):1-8, (2013).
WIPO Application No. PCT/IB2012/053178, PCT International Preliminary Report on Patentability mailed Jan. 9, 2014.
WIPO Application No. PCT/IB2012/053178, PCT International Search Report and Written Opinion of the International Searching Authority mailed Oct. 10, 2012.
WIPO Application No. PCT/IB2012/057259, PCT International Preliminary Report on Patentability mailed Jun. 26, 2014.
WIPO Application No. PCT/IB2012/057259, PCT International Search Report and Written Opinion of the International Searching Authority mailed Apr. 12, 2013.
WIPO Application No. PCT/US2010/038200, International Search Report and Written Opinion of the International Searching Authority, mailed Jun. 10, 2010.
WIPO Application No. PCT/US2010/038200, PCT International Preliminary Report on Patentability mailed Dec. 22, 2011.
Zaleska et al., "The development of stroke therapeutics: Promising mechanisms and translational challenges," Neuropharmacology, 56:329-341, (2009).
"Activase (Alteplase) Full Prescribing Information ," Genentech, Inc., 16 pages, (2015).
Fisher et al., "Current Concepts of the Ischemic Penumbra: Introduction ," Stroke, 35:2657-2658, (2004).
Gerraty et al., "Examining the Lacunar Hypothesis With Diffusion and Perfusion Magnetic Resonance Imaging," Stroke, 33:2019-2024, (2002).
Krams et al., "Acute Stroke Therapy by Inhibition of Neutrophils (ASTIN), An Adaptive Dose-Response Study of UK-279,276 in Acute Ischemic Stroke," Stroke, 34:2543-2548, (2003).
Saver et al., "Alteplase for ischaemic stroke—much sooner is much better," www.thelancet.com, 375:1667-1668, (2010).
U.S. Appl. No. 14/128,941, Final Office Action mailed May 11, 2016.
Wong et al., "Early changes in physiological variables after stroke," Ann Indian Acad Neurol, 11(4): 207-220, (2008).

MODEL SYSTEMS AND TREATMENT REGIMES FOR TREATMENT OF NEUROLOGICAL DISEASE

CROSS-REFERENCE TO RELATED APPLICATIONS

The present application is a continuation of Ser. No. 13/377,523 filed Jun. 11, 2012, which is a national stage entry of PCT/US2010/038200 filed Jun. 10, 2010, which claims priority to 61/185,989 filed Jun. 10, 2009, each incorporated by reference in its entirety for all purposes.

REFERENCE TO A SEQUENCE LISTING

This application includes an electronic sequence listing in a file named 456587_SEQTXT.TXT, created on Jan. 13, 2015 and containing 17,930 bytes which is hereby incorporated by reference.

BACKGROUND OF THE INVENTION

Early work on excitotoxicity suggested that stroke and neurotrauma might be treated using drugs that block glutamate receptors (Albers, Archives in Neurology 49:418-420 (1992); Albers Ann Neurol 25:398-403 (1989)). Although early tests in vitro and in animal models were promising, unfortunately, all clinical stroke trials of glutamate antagonists to date have shown no benefit, and even toxic side effects (Davis et al., Lancet 349:32 (1997); Morris et al., J Neurosurg 91:737-743 (1999); Davis et al., Stroke 31:347-354 (2000); Ikonomidou et al., Proc Natl Acad Sci USA 97:12885-12890 (2000); Lees et al., Lancet 355:1949-1954 (2000)). A likely explanation is that the negative consequences of administering agents that inhibit excitatory neurotransmission in the CNS had outweighed their utility as neuroprotectants (Ikonomidou and Turski, Lancet Neurology 383-386 (2002). Glutamatergic signalling is required for CNS function and therefore, blocking essential excitatory neurotransmission has negative consequences (Ikonomidou, Biochem. Pharmacol. 62:401-405 (2001)). Thus, a more sophisticated approach to treating neuronal death is required to bypass the negative consequences of blocking glutamate receptors.

One of the present inventors has reported that postsynaptic density-95 protein (PSD-95) couples NMDARs to pathways mediating excitotoxicity and ischemic brain damage (Aarts et al., Science 298, 846-850 (2002)). This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and reduced cerebral infarction volume in rats subjected to transient focal cerebral ischemia.

SUMMARY OF THE INVENTION

The invention provides methods of treating or effecting prophylaxis of disease mediated by excitotoxicity, comprising administering to a subject having or at risk of the disease a phainiacological agent that inhibits binding of PSD-95 to NMDAR 2B and/or of PSD-95 to nNOS, wherein when the agent is a peptide having the amino acid sequence YGRKKRRQRRRKLSSIESDV (SEQ ID NO:6), the dose is 2-3 mg/kg, and if the agent is other than the peptide having the amino acid sequence YGRKKRRQRRRKLSSIESDV, the dose delivers the equivalent effective concentration of the agent to 2-3 mg/kg of the peptide having the amino acid sequence YGRKKRRQRRRKLSSIESDV. In some methods, the agent is the peptide having the amino acid sequence YGRKKRRQRRRKLSSIESDV and the dose is 2.6 mg/kg. In some methods, the dose is administered once per episode of the disease. In some methods, the dose is administered without-co-administration of an anti-inflammatory agent.

The invention also provides methods of treating or effecting prophylaxis of a disease mediated by excitotoxicity, comprising administering to a subject having or at risk of the disease a pharmacological agent that inhibits binding of PSD-95 to NMDAR 2B and/or PSD-95 to nNOS, wherein the agent is linked to an internalization peptide, and the agent is administered by intravenous infusion over a period of 5-15 minutes. In some methods, the agent linked to the internationalization peptide is the peptide having the amino acid sequence YGRKKRRQRRRKLSSIESDV (SEQ ID NO:6) and the period is 5 minutes. In some methods, the dose of the pharmacological agent is greater than 1 mg/kg. In some methods, the dose of the pharmacological agent is 2-3 mg/kg. In some methods, the dose of the pharmacological agent is 2.6 mg/kg. In some methods, the dose is up to 50 mg/kg, provided that if the dose is greater than 3 mg/kg the dose is co-administered with an anti-inflammatory. In some methods, is administered without co-administration of an anti-inflammatory agent. In some methods, the subject has a stroke. In some methods, the subject is undergoing surgery, optionally, endovascular surgery to treat an aneurysm.

The invention further provides methods of inhibiting ischemic damage from neurosurgery or endovascular surgery (whether or not in the CNS), comprising administering an effective regime of an agent that inhibits binding of PSD-95 to NMDAR 2B to a patient undergoing neurosurgery. In some methods, the neurosurgery is diagnostic angiography of the brain. In some methods, the neurosurgery is endovascular surgery to treat an aneurysm. In some methods, the agent is administered before the endovascular surgery. In some methods, the agent is administered within 1 hour of completing endovascular surgery. In some methods, the endovascular surgery comprising inserting a coil into the aneurysm. In some methods, the endovascular surgery comprises inserting a stent into the vessel subject to the aneurysm. In some methods, the endovascular surgery comprises inserting a microcatheter.

The invention provides methods of performing a clinical trial on a pharmacological agent comprising administering the pharmacological agent to a population of patients undergoing endovascular surgery for a brain aneurysm, comparing the frequency of a damaging effect of the surgery in the patients compared with control patients undergoing the endovascular surgery without the pharmacological agent, to determine whether the pharmacological agent reduces the damaging effect. In some methods, the damaging effect is assessed by the number and/or size of cerebral infarctions. Some methods further comprise testing the pharmacological agent in an animal model of stroke. Some methods further comprise testing the pharmacological agent in a human patient having a stroke. Some methods further comprise labeling the pharmacological agent for treatment of stroke. In some methods, the pharmacological agent inhibits binding of PSD95 to NMDAR 2B and/or PSD-95 to nNOS.

The invention further provides methods of testing a pharmacological agent. Such methods involve: (a) inserting particles into a cerebral blood vessel of a primate; (b) administering the pharmacological agent to the primate; and (c) comparing a damaging effect in the primate compared to a control primate not treated with the compound. In some methods, the damaging effect is assessed by number and/or size of infarctions. In some methods, the infarctions are determined by MRI or CAT scanning. In some methods, the damaging effect is assessed by a behavioral symptom of the primate compared with the control primate. Some methods further comprise repeating steps (a)-(c) on the same primate after a recovery period provided the agent tested on repeating steps (a)-(c) may or may not be the same as when steps (a)-(c) were previously preformed. Some methods further comprise repeating steps (a)-(c) except that the control primate receives the agent and the animal previously receiving the agent is the control animal. In some methods, the agent inhibits binding of PSD-95 to NMDAR 2B and/or PSD-95 to nNOS. Some methods further comprise administering the agent to a human stroke subject. Some methods further comprise administering the agent to a human subject undergoing endovascular surgery for an aneurysm. In some methods, the agent is administered after inserting particles into the cerebral blood vessel. In some methods, the agent is administered before inserting particles into the cerebral blood vessel. In some methods, the particles are 100 micron polystyrene spheres. In some methods, 20 spheres are administered to the primate. In some methods, the primate is a macaque.

The invention further provides a lyophilized composition comprising the peptide having the amino acid sequence YGRKKRRQRRRKLSSIESDV (SEQ ID NO:6) lyophilized from a solution of the peptide in normal saline prepared under GMP conditions.

The invention further provides a method of storing a pharmaceutical composition comprising storing a pharmaceutical composition comprising a peptide having the amino acid sequence YGRKKRRQRRRKLSSIESDV (SEQ ID NO:6) at concentration of 10-30 mg/ml in normal saline under GMP conditions at below 0° C. for a period of at least two years. Optionally the concentration is 18-20 mg/ml. Some methods further comprise administering the pharmaceutical composition to a patient.

DEFINITIONS

Figure 1:
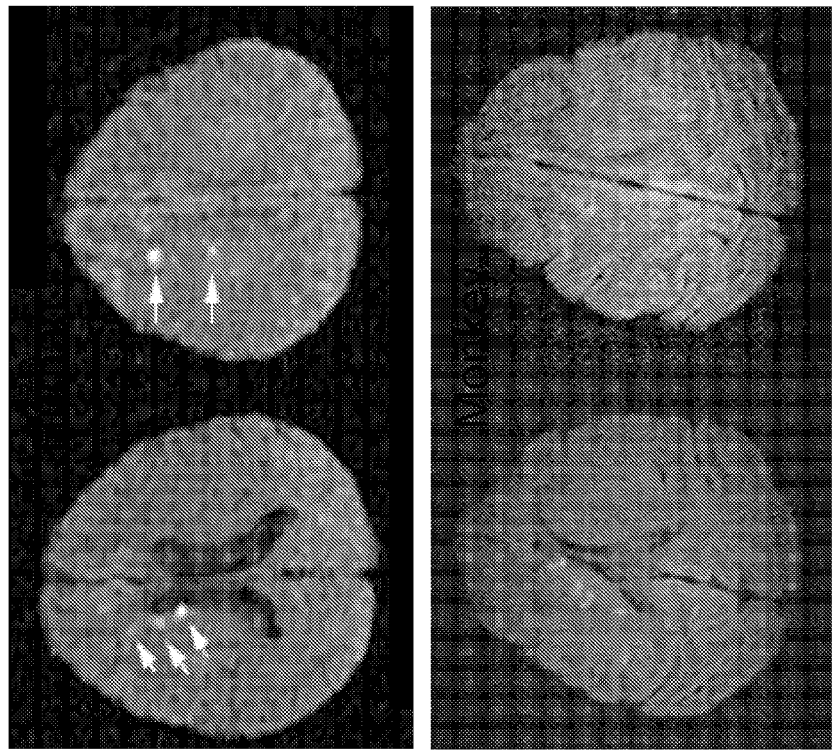
FIG. 1 shows a diffusion-weighted MRI scan of infarctions 24 hr post injection of spheres in a control animal compared with a human having received endovascular surgery to insert a coil to repair an aneurysm. The upper portion shows diffusion defects 48 hours post aneurysm coiling in a 44 year old female human. The lower portion shows diffusion defects 24 hours post injection of 20×100 um polystyrene microspheres in a male cynomolgus macaque.

A "chimeric peptide" means a peptide having two component peptides not naturally associated with one another joined to one another as a fusion protein or by chemical linkage.

A "fusion" protein or polypeptide refers to a composite polypeptide, i.e., a single contiguous amino acid sequence, made up of sequences from two (or more) distinct, heterologous polypeptides which are not normally fused together in a single polypeptide sequence.

The term "PDZ domain" refers to a modular protein domain of about 90 amino acids, characterized by significant sequence identity (e.g., at least 60%) to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, Cell 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 9, 10, 12, 14 or 16 residues), forms such a molecular complex. The molecular complex can be observed in vitro using the "A assay" or "G assay" described, e.g., in U.S. application Ser. No. 10/714,537, or in vivo.

The term "NMDA receptor," or "NMDAR," refers to a membrane associated protein that is known to interact with NMDA including the various subunit forms described below. Such receptors can be human or non-human (e.g., mouse, rat, rabbit, monkey).

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species. The term isolated or purified does not necessarily exclude the presence of other components intended to act in combination with an isolated species. For example, an internalization peptide can be described as isolated notwithstanding that it is linked to an active peptide.

A "peptidomimetic" refers to a synthetic chemical compound which has substantially the same structural and/or functional characteristics of a peptide consisting of natural amino acids. The peptidomimetic can contain entirely synthetic, non-natural analogues of amino acids, or can be a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. In a peptidomimetic of a chimeric peptide comprising an active peptide and an internalization peptide, either the active moiety or the internalization moiety or both can be a peptidomimetic.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Excitotoxicity is the pathological process by which neurons are damaged and killed by the overactivation of receptors for the excitatory neurotransmitter glutamate, such as the NMDA receptors, e.g., NMDAR 2B.

The term "subject" or "patient" includes humans and veterinary animals, such as mammals.

The term "agent" includes any compound including compounds with or without pharmaceutical activity, natural compounds, synthetic compounds, small molecules, peptides and peptidomimetics.

The term "pharmacologic agent" means an agent having a pharmacological activity. Pharmacological agents include compounds that are known drugs, compounds for which pharmacological activity has been identified but which are undergoing further therapeutic evaluation in animal models or clinical trials. A chimeric agent comprises a pharmacologic agent linked to an internalization peptide. An agent can be described as having pharmacological activity if it exhibits an activity in a screening system that indicates that the active agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

A tat peptide means a peptide comprising or consisting of GRKKRRQRRR (SEQ ID NO:1), in which no more than 5 residues are deleted, substituted or inserted within the sequence, which retains the capacity to facilitate uptake of a linked peptide or other agent into cells. Preferably any amino acid changes are conservative substitutions. Preferably, any substitutions, deletions or internal insertions in the aggregate leave the peptide with a net cationic charge, preferably similar to that of the above sequence. The amino acids of a tat peptide can be derivatized with biotin or similar molecule to reduce an inflammatory response.

Co-administration of a pharmacological agents linked to an internalization peptide and an anti-inflammatory agent means that the two agents are administered sufficiently proximately in time that the anti-inflammatory agent can inhibit an inflammatory response inducible by the internalization peptide.

Statistically significant refers to a p-value that is <0.05, preferably <0.01 and most preferably <0.001.

An episode of a disease means a period when signs and/or symptoms of the disease are present interspersed by flanked by longer periods in which the signs and/or symptoms or absent or present to a lesser extent.

DETAILED DESCRIPTION OF THE INVENTION

I. General

The invention provides animal models and clinical trials for assessing agents for potential use in treating or effecting prophylaxis for stroke and other neurological diseases, particularly those mediated at least in part by excitotoxicity. The invention also provides preferred dosage and infusion regimes and pharmaceutical compositions for clinical application of such agents.

II. Agents for Treating Disease

Although any agents can be screened for efficacy in the animal models or clinical trials described below, including agents that have failed previous clinical trials for stroke, a preferred class of agents inhibits interactions between PSD-95 and one or more NMDARs. Such agents are useful for reducing damaging effects of stroke and other neurological conditions mediated at least in part by NMDAR excitotoxicity. Such agents include peptides having an amino acid sequence including or based on the PL motif of a NMDA Receptor or PDZ domain of PSD95. Such peptides can also inhibit interactions between PSD-95 and nNOS and other glutamate receptors (e.g., kainite receptors or AMPA receptors), such as KV1-4 and GluR6. Preferred peptides inhibit interaction between PDZ domains 1 and 2 of postsynaptic density-95 protein (PSD-95)(human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:11) and a PL motif ESDV (SEQ ID NO:12). Preferred peptides inhibit the human forms of PSD-95 and human NMDAR receptors. However, inhibition can also be shown from species variants of the proteins. A list of NMDA and glutamate receptors that can be used appears below:

TABLE 1

NMDA Receptors With PL Sequences

| Name | GI or Acc# | C-terminal 20 mer sequence | C-terminal 4 mer sequence | PL? | internal PL ID |
|---|---|---|---|---|---|
| NMDAR1 | 307302 | HPTDITGPLNLSDPSVSTVV (SEQ ID NO: 13) | STVV (SEQ ID NO: 27) | X | AA216 |

TABLE 1 -continued

NMDA Receptors With PL Sequences

| Name | GI or Acc# | C-terminal 20 mer sequence | C-terminal 4 mer sequence | PL? | internal PL ID |
|---|---|---|---|---|---|
| NMDAR1-1 | 292282 | HPTDITGPLNLSDPSVSTVV (SEQ ID NO: 13) | STVV (SEQ ID NO: 27) | X | AA216 |
| NMDAR1-4 | 472845 | HPTDITGPLNLSDPSVSTVV (SEQ ID NO: 13) | STVV (SEQ ID NO: 27) | X | AA216 |
| NMDAR1-3b | 2343286 | HPTDITGPLNLSDPSVSTVV (SEQ ID NO: 13) | STVV (SEQ ID NO: 27) | X | AA216 |
| NMDAR1-4b | 2343288 | HPTDITGPLNLSDPSVSTVV (SEQ ID NO: 13) | STVV (SEQ ID NO: 27) | X | AA216 |
| NMDAR1-2 | 11038634 | RRAIEREEGQLQLCSRHRES (SEQ ID NO: 14) | HRES (SEQ ID NO: 28) | | |
| NMDAR1-3 | 11038636 | RRAIEREEGQLQLCSRHRES (SEQ ID NO: 14) | HRES (SEQ ID NO: 28) | | |
| NMDAR2C | 6006004 | TQGFPGPCTWRRISSLESEV (SEQ ID NO: 15) | ESEV (SEQ ID NO: 29) | X | AA180 |
| NMDAR3 | 560546 | FNGSSNGHVYEKLSSIESDV (SEQ ID NO: 11) | ESDV (SEQ ID NO: 12) | X | AA34.1 |
| NMDAR3A | 17530176 | AVSRKTELEEYQRTSRTCES (SEQ ID NO: 16) | TCES (SEQ ID NO: 30) | | |
| NMDAR2B | 4099612 | FNGSSNGHVYEKLSSIESDV (SEQ ID NO: 11) | ESDV (SEQ ID NO: 12) | X | |
| NMDAR2A | 558748 | LNSCSNRRVYKKMPSIESDV (SEQ ID NO: 17) | ESDV (SEQ ID NO: 12) | X | AA34.2 |
| NMDAR2D | 4504130 | GGDLGTRRGSAHFSSLESEV (SEQ ID NO: 18) | ESEV (SEQ ID NO: 29) | X | |
| Glutamate receptor delta 2 | AF009014 | QPTPTLGLNLGNDPDRGTSI (SEQ ID NO: 19) | GTSI (SEQ ID NO: 31) | X | |
| Glutamate receptor 1 | I28953 | MQSIPCMSHSSGMPLGATGL (SEQ ID NO: 20) | ATGL (SEQ ID NO: 32) | X | |
| Glutamate receptor 2 | L20814 | QNFATYKEGYNVYGIESVKI (SEQ ID NO: 21) | SVKI (SEQ ID NO: 33) | X | |
| Glutamate receptor 3 | AF167332 | QNYATYREGYNVYGTESVKI (SEQ ID NO: 22) | SVKI (SEQ ID NO: 33) | X | |
| Glutamate receptor 4 | U16129 | HTGTAIRQSSGLAVIASDLP (SEQ ID NO: 23) | SDLP (SEQ ID NO: 34) | | |
| Glutamate receptor 5 | U16125 | SFTSILTCHQRRTQRKETVA (SEQ ID NO: 24) | ETVA (SEQ ID NO: 35) | X | |
| Glutamate receptor 6 | U16126 | EVINMHTFNDRRLPGKETMA (SEQ ID NO: 25) | ETMA (SEQ ID NO: 36) | X | |

Some peptides inhibit interactions between PSD-95 and multiple NMDAR subunits. In such instances, use of the peptide does not necessarily require an understanding of the respective contributions of the different NMDARs to excitatory neurotransmission. Other peptides are specific for a single NMDAR.

Peptides can include or be based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T]-[D/E/Q/N]-[V/L] (SEQ ID NO:38) at their C-terminus. Exemplary peptides comprise: ESDV (SEQ ID NO:12), ESEV (SEQ ID NO:29), ETDV (SEQ ID NO:39), ETEV (SEQ ID NO:40), DTDV (SEQ ID NO:41), and DTEV (SEQ ID NO:42) as the C-terminal amino acids. Two particularly preferred peptides are KLSSIESDV (SEQ ID NO:5), and KLSSIETDV (SEQ ID NO:43). Such peptides usually have 3-25 amino acids (without an internalization peptide), peptide lengths of 5-10 amino acids, and particularly 9 amino acids (also without an internalization peptide) are preferred. In some such peptides, all amino acids are from the C-terminus of an NMDA receptor (not including amino acids from an internalization peptide).

Other peptides that inhibit interactions between PDS95 and NDMARs include peptides from PDZ domain 1 and/or 2 of PSD-95 or a subfragment of any of these that inhibits interactions between PSD-95 and an NMDA receptor, such as NMDA 2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1):71-82 (1997) (human sequence) or NP_031890.1, GI:6681195 (mouse sequence) or corresponding regions of other species variants.

Peptides and peptidomimetics of the invention can contain modified amino acid residues for example, residues that are N-alkylated. N-terminal alkyl modifications can include e.g., N-Methyl, N-Ethyl, N-Propyl, N-Butyl, N-Cyclohexylmethyl, N-Cyclyhexylethyl, N-Benzyl, N-Phenylethyl, N-phenylpropyl, N-(3, 4-Dichlorophenyl)propyl, N-(3,4-Difluorophenyl)propyl, and N-(Naphthalene-2-yl)ethyl).

Bach, J. Med. Chem. 51, 6450-6459 (2008) and WO 2010/004003 has described a series of analogs of NMDAR 2B 9c. PDZ-binding activity is exhibited by peptides having only three C-terminal amino acids (SDV). Bach also reports analogs having an amino acid sequence comprising or consisting of YtSXV (SEQ ID NO:68), wherein t and S are alternative amino acids, Y is selected from among E, Q, and A, or an analogue thereof, X is selected from among A, Q, D, N, N-Me-A, N-Me-Q, N-Me-D, and N-Me-N or an analogue thereof. Optionally the peptide is N-alkylated in position P3 position (third amino acid from C-terminus, i.e. position occupied by tS). The peptide can be N-alkylated with a cyclohexane or aromatic substituent, and further comprises a spacer group between the substituent and the terminal amino group of the peptide or peptide analogue, wherein the spacer is an alkyl group, preferably selected from among methylene, ethylene, propylene and butylene. The aromatic substituent can be a naphthalen-2-yl moiety or an aromatic ring substituted with one or two halogen and/or alkyl group.

Other modifications can also be incorporated without adversely affecting the activity and these include substitution of one or more of the amino acids in the natural L-isomeric form with amino acids in the D-isomeric form. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form. Thus, a peptidomimetic may include 1, 2, 3, 4, 5, at least 50%, or all D-amino acid resides. A peptidomimetic containing some or all D residues is sometimes referred to an "inverso" peptide.

Peptidomimetics also include retro peptides. A retro peptide has a reverse amino acid sequence. Peptidomimetics also include retro inverso peptides in which the order of amino acids is reversed from so the originally C-terminal amino acid appears at the N-terminus and D-amino acids are used in place of L-amino acids. WO 2008/014917 describes a retro-inverso analog of Tat-NR2B9c having the amino acid sequence vdseisslk-rrrqrrkkrgyin (SEQ ID NO:69) (lower case letters indicating D amino acids), and reports it to be effective inhibiting cerebral ischemia. Another effect peptide described herein is Rv-Tat-NR2B9c (RRRQRRK-KRGYKLSSIESDV; SEQ ID NO:70).

A linker, e.g., a polyethylene glycol linker, can be used to dimerize the active moiety of the peptide or the peptidomimetic to enhance its affinity and selectivity towards proteins containing tandem PDZ domains. See e.g., Bach et al., (2009) Angew. Chem. hit. Ed. 48:9685-9689 and WO 2010/004003. A PL motif-containing peptide is preferably dimerized via joining the N-termini of two such molecules, leaving the C-termini free. Bach further reports that a pentamer peptide IESDV (SEQ ID NO:71) from the C-terminus of NMDAR 2B was effective in inhibiting binding of NMDAR 2B to PSD95. Optionally, about 2-10 copies of a PEG can be joined in tandem as a linker.

Appropriate pharmacological activity of peptides, peptidomimetics or other agent can be confirmed if desired, using previously described rat models of stroke before testing in the primate and clinical trials described in the present application. Peptides or peptidomimetics can also be screened for capacity to inhibit interactions between PSD-95 and NMDAR 2B using assays described in e.g., US 20050059597, which is incorporated by reference. Useful peptides typically have IC50 values of less than 50 μM, 25 μM, 10 μM, 0.1 μM or 0.01 μM in such an assay. Preferred peptides typically have an IC50 value of between 0.001-1 μM, and more preferably 0.05-0.5 or 0.05 to 0.1 μM. When a peptide or other agent is characterized as inhibiting binding of one interaction, e.g., PSD-95 interaction to NMDAR2B, such description does not exclude that the peptide or agent also inhibits another interaction, for example, inhibition of PSD-95 binding to nNOS.

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Pharmacological agents also include small molecules that inhibit interactions between PSD95 and NMDAR 2B, and/or other interactions described above. Suitable small-molecule inhibitors are described in WO/2009/006611. An exemplary class of suitable compounds are of the formula:

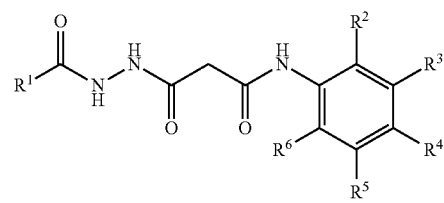

wherein $R^1$ is a member selected from the group consisting of cyclohexyl substituted with 0-4 $R^7$, phenyl substituted with 0-4 $R^7$, —(CH$_2$)$_u$—(CHR$^8$R$^9$), a branched C$_{1-6}$ alkyl (isopropyl, isobutyl, 1-isopropyl-2-methyl-butyl, 1 ethylpropyl), and —NH—C(O)—(CR$^{10}$R$^{11}$)$_x$H;

each $R^7$ is independently a member selected from the group consisting of C$_{1-6}$ alkyl, C$_{1-6}$ alkoxy, —C(O)R$^{12}$, OH, COOH, —NO, N-substituted indoline and a cell membrane translocation peptide;

each $R^8$ and $R^9$ is independently selected from the group consisting of H, OH, cyclohexane, cyclopentane, phenyl, substituted phenyl and cyclopentadiene;

each $R^{10}$ and $R^{11}$ is independently selected from the group consisting of H, cyclohexane, phenyl and a cell membrane translocation peptide;

$R^{12}$ is a member selected from the group consisting of $C_{1-6}$ alkyl and aryl; and each of u and v are independently from 0 to 20;

wherein one of $R^2$, $R^3$, $R^4$, $R^5$ and $R^6$ is —COOH, and wherein the remainder of $R^2$, $R^3$, $R^4$, $R^5$ and $R^6$ are each independently selected from the group consisting of F, H, $OCH_3$ and $CH_3$.

One such compound is 0620-0057, the structure of which is:

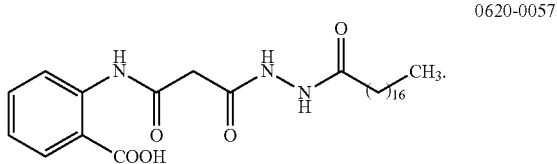

0620-0057

A pharmacological agent can be linked to an internalization peptide to facilitate uptake into cells and/or across the blood brain barrier. Internalization peptides are a well-known class of relatively short peptides that allow many cellular or viral proteins to traverse membranes. Internalization peptides, also known as cell membrane transduction peptides or cell penetrating peptides can have e.g., 5-30 amino acids. Such peptides typically have a cationic charge from an above normal representation (relative to proteins in general) of arginine and/or lysine residues that is believed to facilitate their passage across membranes. Some such peptides have at least 5, 6, 7 or 8 arginine and/or lysine residues. Examples include the antennapedia protein (Bonfanti, Cancer Res. 57, 1442-6 (1997)) (and variants thereof), the tat protein of human immunodeficiency virus, the protein VP22, the product of the UL49 gene of herpes simplex virus type 1, Penetratin, SynB1 and 3, Transportan, Amphipathic, gp41NLS, polyArg, and several plant and bacterial protein toxins, such as ricin, abrin, modeccin, diphtheria toxin, cholera toxin, anthrax toxin, heat labile toxins, and Pseudomonas aeruginosa exotoxin A (ETA). Other examples are described in the following references (Temsamani, Drug Discovery Today, 9(23):1012-1019, 2004; De Coupade, Biochem J., 390:407-418, 2005; Saalik Bioconjugate Chem. 15: 1246-1253, 2004; Zhao, Medicinal Research Reviews 24(1):1-12, 2004; Deshayes, Cellular and Molecular Life Sciences 62:1839-49, 2005) (all incorporated by reference).

A preferred internalization peptide is tat from the HIV virus. A tat peptide reported in previous work comprises or consists of the standard amino acid sequence YGRKKRRQRRR (SEQ ID NO:2) found in HIV Tat protein. If additional residues flanking such a tat motif are present (beside the pharmacological agent) the residues can be for example natural amino acids flanking this segment from a tat protein, spacer or linker amino acids of a kind typically used to join two peptide domains, e.g., gly (ser)$_4$ (SEQ ID NO:44), TGEKP (SEQ ID NO:45), GGRRGGGS (SEQ ID NO:46), or LRQRDGERP (SEQ ID NO:47) (see, e.g., Tang et al. (1996), J. Biol. Chem. 271, 15682-15686; Hennecke et al. (1998), Protein Eng. 11, 405-410)), or can be any other amino acids that do not significantly reduce capacity to confer uptake of the variant without the flanking residues. Preferably, the number of flanking amino acids other than an active peptide does not exceed ten on either side of YGRKKRRQRRR (SEQ ID NO:2). One suitable tat peptide comprising additional amino acid residues flanking the C-terminus of YGRKKRRQRRR (SEQ ID NO:2) is YGRKKRRQRRRPQ (SEQ ID NO:48). However, preferably, no flanking amino acids are present. Other tat peptides that can be used include GRKKRRQRRRPQ (SEQ ID NO:4) and GRKKRRQRRRP (SEQ ID NO:72).

Variants of the above tat peptide having reduced capacity to bind to N-type calcium channels are described by WO/2008/109010. Such variants can comprise or consist of an amino acid sequence XGRKKRRQRRR (SEQ ID NO:49), in which X is an amino acid other than Y or nothing (in which case G is a free N-terminal residue). A preferred tat peptide has the N-terminal Y residue substituted with F. Thus, a tat peptide comprising or consisting of FGRKKRRQRRR (SEQ ID NO:3) is preferred. Another preferred variant tat peptide consists of GRKKRRQRRR (SEQ ID NO:1). Another preferred tat peptide comprises or consists of RRRQRRKKRG (amino acids 1-11 of SEQ ID NO:70). Other tat derived peptides that facilitate uptake of a pharmacological agent without inhibiting N-type calcium channels include those presented in Table 2 below.

TABLE 2

X-FGRKKRRQRRR (F-Tat) (SEQ ID NO: 3)

X-GKKKKKQKKK (SEQ ID NO: 50)

X-RKKRRQRRR (SEQ ID NO: 51)

X-GAKKRRQRRR (SEQ ID NO: 52)

X-AKKRRQRRR (SEQ ID NO: 53)

X-GRKARRQRRR (SEQ ID NO: 54)

X-RKARRQRRR (SEQ ID NO: 55)

X-GRKKARQRRR (SEQ ID NO: 56)

X-RKKARQRRR (SEQ ID NO: 57)

X-GRKKRRQARR (SEQ ID NO: 58)

X-RKKRRQARR (SEQ ID NO: 59)

X-GRKKRRQRAR (SEQ ID NO: 60)

X-RKKRRQRAR (SEQ ID NO: 61)

X-RRPRRPRRPRR (SEQ ID NO: 62)

X-RRARRARRARR (SEQ ID NO: 63)

X-RRRARRRARR (SEQ ID NO: 64)

X-RRRPRRRPRR (SEQ ID NO: 65)

X-RRPRRPRR (SEQ ID NO: 66)

X-RRARRARR (SEQ ID NO: 67)

X can represent a free amino terminus, one or more amino acids, or a conjugated moiety. Internalization peptides can be used in inverso or retro or inverso retro form with or without the linked peptide or peptidomimetic being in such form. For example, a preferred chimeric peptide has an amino acid sequence comprising or consisting of RRRQRRKKRGY-KLSSIESDV (SEQ ID NO:70).

Internalization peptides can be attached to pharmacological agents by conventional methods. For example, the agents can be joined to internalization peptides by chemical linkage, for instance via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene) bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m, m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

For pharmacological agents that are peptides attachment to an internalization peptide can be achieved by generating a fusion protein comprising the peptide sequence fused, preferably at its N-terminus, to an internalization peptide.

Pharmacologic peptides, optionally fused to tat peptides, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

III. Non-Human Primate Model

As discussed in the Background section, several previous clinical trials of pharmacological agents for treating stroke have failed notwithstanding that the agents have shown promising results in lower animal models of stroke, such as the rat. Performing similar model experiments on non-human primates would provide a better indicator of how an agent would perform in humans and thus possibly save the effort and expense of an unsuccessful clinical trial. However, the types of experiments performed on rats usually involve sacrificing the animal and would thus be unethical and/or prohibitively expensive to perform on primates to the extent necessary to evaluate an agent.

The present application provides a primate model of cerebral ischemic disease that does not require sacrifice of the primate and results in little if any permanent harm to the primate. Cerebral ischemia is induced by introducing particles into a cerebral blood vessel of a primate. The particles can be introduced by endovascular surgery analogous to that performed on human subjects receiving such surgery for treatment of aneurysm. The particles used can be about 50-200 and preferably 75-150 or 100 microns in diameter. The number of particles introduced can be e.g., 1-100, or 10-30 with about 20 per animal being preferred. The number and size of particles increase the severity of the stroke(s). For example, a particle size of 400 microns can cause strokes so large animals may not recover. Polystyrene microspheres from Polysciences, Inc. are suitable. Any type of non-human primate, such as macaque, marmoset, baboon or chimpanzee, can be used in the model. Any agent can be tested including those described above or previously tested in animal models or clinical trials in the art.

The effect of introducing the particles can be assessed by for example, MRI, CAT scanning and/or behaviorally. MRI analysis shows that introducing the particles usually induces several small infarctions around the site of the particles. MRI analysis is preferably diffusion weighted (DW-MRI). Diffusion-weighted MRI is a standard technique for imaging stroke in which infarctions appear darker than surrounding tissue. The use of a bipolar gradient pulse and suitable pulse sequences permits the acquisition of diffusion weighted images (images in which areas of rapid proton diffusion can be distinguished from areas with slow diffusion).diffusion-weighted images are very helpful to identify any area of acute ischemia and to separate the acute infarction from old strokes and other chronic changes in the brain. Only the acute infarcts appear hyperintense on the diffusion images.

The appearance of the infarction is similar to infarctions often found in human subjects undergoing endovascular surgery to repair an aneurysm. Infarctions can be assessed, for example, after 4 hr, 24 hr or 14 days after introducing the particles. Typically injecting twenty 100 micron microspheres produces between 12 and 14 infarcts detectable by MRI imaging. The typical brain volume occupied by such infarcts is about 5-10 mm$^3$ each, or at total of about 60-70+/−30 mm$^3$. In human subjects undergoing endovascular surgery infarcts are larger, typically 5-10 mm in diameter corresponding to about 0.5 to 1.5 cm$^3$ each A pharmacological agent can be administered to the primate before, during or after introduction of the particles. In some methods, the pharmacological agent is administered within a window of 0-3 or 1-3 hr after introducing the particles. In other methods, the pharmaceutical agent is administered 0-3 hours before introducing the particles. Vehicle (e.g., PBS) is usually administered to a control primate also receiving the particles in parallel with administration of the pharmacological agent.

The effects of treatment are assessed by comparing number, volume and/or appearance of infarctions and/or behavioral characteristics between a treated primate or population of treated primates and a control or population of control primates. A reduction in number and/or volume of infarctions in the treated primate(s) relative to control primate(s) indicates the agent has activity potentially useful in treating stroke and other diseases mediated in part by excitotoxicity.

A variety of methods have been described for assessing cognitive function or neurological damage in non-human primates (see Marshall et al., *Stroke* 2003; 34:2228-2233; *Stroke* 2001; 32:190-198; *Brain Res Bull* 2003; 61:577-585; Hatsopoulos et al., *Proc Natl Acad Sci USA* 1998; 95:15706-15711; Spetzler et al., *Neurosurgery* 1980; 7:257-261; Barbay et al., *Exp Brain Res* 2006; 169:106-116. An exemplary experiment involves conditioning monkeys to use their upper limb to visually guide a cursor on a computer screen using planar reaching movements from a central holding position to a radially located target position. The time to move the cursor to the target provides a measure of cognitive function or conversely neurological damage.

After analysis of treated and control animals is complete, the animals are given a period to recover during which the diffusion weighted MRI signal from the infarctions disappears. This period is typically about 10-14 days. After about 14-28 days after initially inserting the beads, the protocol is repeated optionally, with the treated animals serving as controls and vice versa. The cross-repetition of the protocol between treated and control animal serves to eliminate any bias of the results due to anomalies of particular animals. According to such a repeated protocol, reliable results can be obtained from a trial involving only ten primates. Each primate can undergo at least five cycles of particle insertion and then continue to live normal lives with little if any permanent neurological damage.

The experimental model is particularly useful for assessing pharmacological agents for use in treating stroke and for use as an adjunct in method of surgery involving any manipulation of blood vessels supplying the brain, particularly in endovascular repair of brain aneurysm. The trial also provides a useful indication of the suitability of a pharmacological agent for use in treating other diseases and disorders characterized by cerebral ischemia and/or mediated by excitotoxity. If a pharmacological agent inhibits development of infarctions or neurological behavioral impairment in the primate trial, the agent can be tested in human clinical trials, for example, a trial in stroke subjects, or on subjects undergoing endovascular repair of a brain aneurysm.

IV. Clinical Trial

Procedures that involve manipulating the great vessels, such as the aortic arch (cardiopulmonary bypass), and procedures in which catheters are introduced into the cervical carotid arteries, such as diagnostic and therapeutic cerebral angiograms, commonly dislodge embolic materials that may lead to ischemic strokes of varying frequency and severity (reviewed by Bendszus, Lancet Neurol 2006 April; 5(4): 364-72 2006). For example, in a representative study of thirty-five consecutive subjects undergoing elective coronary artery bypass grafting (CABG), diffusion-weighted magnetic resonance imaging demonstrated new ischemic lesions in 9 (26%) of the subjects (Bendszus et al., Arch. Neurol. 59 (7):1090-1095, 2002), with such estimates of new lesions by diffusion-weighted MRI (DWI-MRI) ranging in the literature up to 45% in CABG subjects (Knipp et al., Eur. J. Cardiothorac. Surg. 25 (5):791-80.0 2004) and 47% in subjects undergoing cardiac valve repairs (Knipp et al., Eur. J. Cardiothorac. Surg. 28 (1):88-96 2005). The majority of subjects exhibit two or more lesions (Knipp et al., 2004, supra). This effect is seen in subjects undergoing either on-pump or off-pump CABG, probably because it is the manipulation of the great vessels that is critical for dislodging damaging emboli.

Cerebral angiography is, in itself, causative of strokes. Bendszus et al. Lancet 354 (9190):1594-1597 (1999) carried out similar studies in subjects undergoing diagnostic or interventional cerebral angiography.

In a prospective study of 100 consecutive angiographies (66 diagnostic and 34 interventional procedures) were done on 91 subjects, diffusion-weighted magnetic resonance imaging (MRI) was performed before and after angiography to assess embolic events was performed. Before angiography, no abnormalities were seen on diffusion weighted MRI. Diffusion-weighted MRI showed 42 bright lesions in 23 subjects after 23 procedures (17 diagnostic, six interventional) in a pattern consistent with embolic events.

After diagnostic angiography in subjects with a history of vasculopathy, the frequency of lesions was significantly higher than in subjects without vascular risk factors (44% vs. 13%, p=0.03). Endovascular aneurysm coiling increases dramatically the risk of procedural strokes compared with diagnostic angiography. In a prospective study, Cronqvist et al., Neuroradiology 47(11):855-73 (2005) demonstrated 47 new ischemic strokes in 37 of 40 subjects (92.5%) undergoing endovascular aneurysm repair. In a study performed on 47 subjects undergoing neurointerventional repair of brain aneurysms at the University Health Network, the incidence of small ischemic strokes detected by DWI-MRI imaging was 75%, with most subjects experiencing at least two embolic events. In the majority of cases, the strokes that occur after angiography or cardiopulmonary bypass are small-volume round lesions, <20 mm in diameter, with an appearance similar to that of lacunar strokes. Although they generally do not produce immediate postprocedural deficits, a significant literature now strongly links small strokes acquired throughout life with deteriorations in cognition, early onset vascular dementias and Alzheimer's disease (Devasenapathy and Hachinski, Options Neuro12:61-72 (2000); Merino and Hachinski, Curr Atheroscler Rep 4:285-290 (2002); Di and Hachinski, Curr Opin Investig Drugs 4:1082-1087 (2003); Del et al., J Neurol Sci 231:3-11 (2005); Hachinski, Stroke 38:1396 (2007).

Acute ischemic strokes afflict an elderly patient population who commonly have medical co-morbidities such as ischemic heart disease, diabetes, hypertension, and other disorders whose prevalence rises in later decades. The patient population is therefore more vulnerable to drug toxicity than is generally the case in other clinical trial. Another difficulty in conducting a clinical trial on patients suffering from acute ischemic strokes is that they must be enrolled in trials within a restricted time window, do not uniformly receive invasive monitoring, and generally are not cared for by anesthesiologists at the outset. In the past, some clinical trials for acute ischemic stroke have had to be stopped due to safety issues arising in Phase 3, despite apparent tolerability of the candidate drug in earlier trials.

Patients who are undergoing surgery for intracranial aneurysms provide a suitable patient population to test the effects of pharmacological agents and represent a further unmet medical need. Such patients are usually elderly (the incidence of aneurysm diagnosis peaks in the 6th and 7th decades), thus recapitulating the age-range of the patient population that is most commonly afflicted by acute ischemic stroke. As discussed above, the vast majority develop at least one small infarction. Moreover, the standard of care for aneurysm patients normally includes constant monitoring by an anesthesiologist, cardiac monitoring with an ECG, and invasive monitoring, entailing arterial lines for constant blood pressure monitoring and central (right atrial) lines when deemed necessary, constant monitoring of blood oxygen saturation and periodic measurements of arterial blood gases ($O_2$, $PCO_2$, pH) and, if needed, serum glucose and electrolytes. Drug administration can take place under conditions of endotracheal intubation and artificial ventilation, providing the ultimate safety scenario in the event of cardio-respiratory compromise, and enabling ultimate control of all cardiac and ventilatory parameters. The drug administration and recovery can be done in an environment where the patient have 1:1 care by an anesthesiologist and other medical and paramedical staff, including nursing. The feasibility of increased monitoring and other safety provisions in a clinical trial provides more opportunity to detect and address any adverse events without terminating the clinical trial.

The clinical trial can be performed on any population of patients undergoing a surgical procedure on a blood vessel supplying the brain (that is connecting the brain to the heart, for example, carotid arteries and jugular veins) or on the brain or CNS itself associated with measurable development of infarctions, such as those described above. Clinical trials can also be performed on patients undergoing an endovascular procedure on an artery supplying blood to the retina, kidney, spinal cord or limbs. A preferred class of patients are those undergoing endovascular surgery to treat a brain aneurysm. The endovascular surgery can entail for example introducing coils into the aneurysm or a stent into the blood vessel to which the aneurysm is attached. The agent can be administered before, during or after the endovascular surgery is completed. A preferred window for administration is from 30 minutes before to 1 hour after completing the endovascular surgery. For example, the pharmacological agent can be administered with 0-30 minutes of completion of surgery. The clinical trial is preferably a control trial in which some patients received a pharmacological agent and other patients receive a placebo or vehicle lacking the pharmacological agent. The effects of treatment with the pharmacological agent can be assessed by reduction in the number and/or volume of infarctions in the treated patients relative to the control population. Infarctions can be assessed in the brain or other tissues, such as retina, kidney, spinal cord and limbs (e.g., by MRI) in comparison with placebo treated patients. Neurological deficits can also be assessed from behavioral characteristics. Pharmacokinetic parameters, such as maximum serum concentration of the drug under test, serum half-life, serum area under curve, and CSF concentration of the drug can also be measured.

Some pharmacological agents tested in such a clinical trial have undergone previous testing in an animal model of stroke or other cerebral ischemic disease. The animal model can be a lower animal model, such as a rat, or a primate model, such as that discussed above. Some agents have also undergone safety evaluation in a phase I human clinical trial such as described in the examples. If a pharmacological agent shows evidence of useful activity in aneurysm patients, the agent can be tested in a clinical trial of acute stroke patients or can be administered to such patients in regular clinical use. The types of pharmacological agent that can be tested include those described above and otherwise tested in the art in animal models of stroke or cerebral ischemic disease or in previous clinical trials.

V. Diseases

The pharmacological agents of the invention are useful in treating a variety of diseases, particularly neurological diseases, and especially diseases mediated in part by excitotoxity. Such diseases and conditions include stroke, epilepsy, hypoxia, traumatic injury to the CNS not associated with stroke such as traumatic brain injury and spinal cord injury, other cerebral ischemia, Alzheimer's disease and Parkinson's disease. Other neurological diseases treatable by agents of the invention not known to be associated with excitotoxicity include anxiety and pain.

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a patient as follows.

TABLE 3

| 0 | No symptoms at all |
| 1 | No significant disability despite symptoms; able to carry out all usual duties and activities. |
| 2 | Slight disability; unable to carry out all previous activities but able to look after own affairs without assistance. |
| 3 | Moderate disability requiring some help, but able to walk without assistance |
| 4 | Moderate to severe disability; unable to walk without assistance and unable to attend to own bodily needs without assistance. |
| 5 | Severe disability; bedridden, incontinent, and requiring constant nursing care and attention. |

The Barthel Index is based on a series of questions about the patient's ability to carry out 10 basic activities of daily living resulting in a score between 0 and 100, a lower score indicating more disability (Mahoney et al., Maryland State Medical Journal 14:56-61 (1965)).

Alternatively stroke severity/outcomes can be measured using the NIH stroke scale, available at world wide web ninds.nih.gov/doctors/NIH_Stroke_Scale_Booklet.pdf.

The scale is based on the ability of a patient to carry out 11 groups of functions that include assessments of the patient's level of consciousness, motor, sensory and language functions.

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms. Patients undergoing heart surgery are at particular risk of transient cerebral ischemic attack.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel ruptures. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

One patient class amenable to treatments are patients undergoing a surgical procedure that involves or may involve a blood vessel supplying the brain, or otherwise on the brain or CNS. Some examples are patients undergoing cardiopulmonary bypass, carotid stenting, diagnostic angiography of the brain or coronary arteries of the aortic arch, vascular surgical procedures and neurosurgical procedures. Additional examples of such patients are discussed in section IV above. Patients with a brain aneurysm are particularly suitable. Such patients can be treated by a variety of surgical procedures including clipping the aneurysm to shut off blood, or performing endovascular surgery to block the aneurysm with small coils or introduce a stent into a blood vessel from which an aneurysm emerges, or inserting a microcatheter. Endovascular procedures are less invasive than clipping an aneurysm and are associated with a better patient outcome but the outcome still includes a high incidence of small infarctions. Such patients can be treated with an inhibitor of PSD95 interaction with NMDAR 2B and particularly the agents described above including the peptide YGRKKRRQRRRKLSSIESDV (SEQ ID NO:6, also known as Tat-NR2B9c). The timing of administration relative to performing surgery can be as described above for the clinical trial.

VI. Effective Regimes of Administration

A pharmacological agents optionally linked to an internalization peptide is administered in an amount, frequency and route of administration effective to cure, reduce or inhibit further deterioration of at least one sign or symptom of a disease in a patient having the disease being treated. Unless otherwise indicated dosages for chimeric agents including a pharmacologic agent linked to an internalization peptide refer to the whole agent rather than just the phainiacological agent component of the chimeric agent. A therapeutically effective amount means an amount of agent sufficient significantly to cure, reduce or inhibit further deterioration of at least one sign or symptom of the disease or condition to be treated in a population of patients (or animal models) suffering from the disease treated with an agent of the invention relative to the damage in a control population of patients (or animal models) suffering from that disease or condition who are not treated with the agent. The amount is also considered therapeutically effective if an individual treated patient achieves an outcome more favorable than the mean outcome in a control population of comparable patients not treated by methods of the invention.

A therapeutically effective regime involves the administration of a therapeutically effective dose at a frequency and route of administration needed to achieve the intended purpose.

For a patient suffering from stroke or other ischemic condition, the agent is administered in a regime comprising an amount frequency and route of administration effective to reduce the damaging effects of stroke or other ischemic condition. When the condition requiring treatment is stroke, the outcome can be determined by infarction volume or disability index, and a dosage is considered therapeutically effective if an individual treated patient shows a disability of two or less on the Rankin scale and 75 or more on the Barthel scale, or if a population of treated patients shows a significantly improved (i.e., less disability) distribution of scores on a disability scale than a comparable untreated population, see Lees et at 1., N Engl J Med 2006; 354:588-600. A single dose of agent is usually sufficient for treatment of stroke.

The invention also provides methods and compositions for the prophylaxis of a disorder in a subject at risk of that disorder. Usually such a subject has an increased likelihood of developing the disorder (e.g., a condition, illness, disorder or disease) relative to a control population. The control population for instance can comprise one or more individuals selected at random from the general population (e.g., matched by age, gender, race and/or ethnicity) who have not been diagnosed or have a family history of the disorder. A subject can be considered at risk for a disorder if a "risk factor" associated with that disorder is found to be associated with that subject. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically. For example, a subject undergoing heart surgery is at risk of transient cerebral ischemic attack because the frequency of transient cerebral ischemic attack is increased in a population of subjects who have undergone heart surgery as compared to a population of subjects who have not.

Other common risk factors for stroke include age, family history, gender, prior incidence of stroke, transient ischemic attack or heart attack, high blood pressure, smoking, diabetes, carotid or other artery disease, atrial fibrillation, other heart diseases such as heart disease, heart failure, dilated cardiomyopathy, heart valve disease and/or congenital heart defects; high blood cholesterol, and diets high in saturated fat, trans fat or cholesterol.

A pharmacological agent optionally linked to an internalization peptide is administered to a patient at risk of a disease but not yet having the disease in an amount, frequency and route sufficient to prevent, delay or inhibit development of at least one sign or symptom of the disease. A prophylactically effective amount means an amount of agent sufficient significantly to prevent, inhibit or delay at least one sign or symptom of the disease in a population of patients (or animal models) at risk of the disease relative treated with the agent compared to a control population of patients (or animal models) at risk of the disease not treated with a chimeric agent of the invention. The amount is also considered prophylactically effective if an individual treated patient achieves an outcome more favorable than the mean outcome in a control population of comparable patients not treated by methods of the invention. A prophylactically effective regime involves the administration of a prophylactically effective dose at a frequency and route of administration needed to achieve the intended purpose. For prophylaxis of stroke in a patient at imminent risk of stroke (e.g., a patient undergoing heart surgery), a single dose of agent is usually sufficient.

Depending on the agent, administration can be parenteral, intravenous, nasal, oral, subcutaneous, intra-arterial, intracranial, intrathecal, intraperitoneal, topical, intranasal or intramuscular. Intravenous administration is preferred for peptide agents.

For chimeric agents including an internalization peptide, particularly a HIV tat peptide comprising the amino acid sequence, administration of the agent may or may not be combined with an anti-inflammatory agent to reduce release or histamine and its downstream effects associated with high levels of the internalization peptide. Preferred agents for co-administration are inhibitors of mast cell degranulation, such as cromolyn or lodoxamide or any others listed herein. Anti-histamines or corticosteroids can also be used, particularly in combinations or higher dosages (see WO2009/076105, 61/185,943; filed: Jun. 10, 2009.

For administration to humans, a preferred dose of the chimeric agent Tat-NR2B9c is 2-3 mg/kg and more preferably 2.6 mg/kg. Indicated dosages should be understood as including the margin of error inherent in the accuracy with which dosages can be measured in a typical hospital setting. The dose is preferred because it is the maximum dose with which the agent can be administered without release of significant amounts of histamine and the ensuing sequelae in most patients. Although release of histamine at higher dosages can be controlled by co-administration of an anti-inflammatory as discussed above and in any event usually spontaneously resolves without adverse events, it is best avoided by keeping the dose below 3 mg/kg and preferably at 2-3 mg/kg, more preferably 2.6 mg/kg. Such amounts are for single dose administration, i.e., one dose per episode of disease.

Histamine release is best avoided not only because of well known sequelae such as reduction in blood pressure, swelling and redness, but because of a report that controlling histamine release can also inhibit development of infarctions in an animal model of stroke (WO 04/071531). Conversely, although lower dosages may well be effective and even preferable in indications having a more chronic course (e.g., anxiety, pain, Alzheimer's, Parkinson's) the extremely acute nature of stroke and similar conditions may leave very little room for a second administration should the first administration prove inadequate or insufficient. Accordingly, in treating acute presentation, it is preferably to administer a single dose at or approaching the level before which significant histamine release occurs in most patients.

The dosages indicated above are for the chimeric agent Tat-NR2B9c (YGRKKRRQRRRKLSSIBSDV; SEQ ID NO:6). Equivalent dosages for other agents to achieve the same effect can be determined by several approaches. For close variants of that agent in which one or a few amino acids are substituted, inserted or deleted and the molecular weight remains the same within about +/−25%, the above dosages are still a good guide. However, in general, for other agents, equivalent dosages can vary depending on the molecular weight of the agent with and without internalization peptide if present, its Kd for its target, and its pharmacokinetic and pharmacodynamic parameters. For some agents, equivalent dosages can be calculated so as to deliver an equimolar amount of the pharmacological agent. For other agent, further adjustment is made to account for differences in Kd or pharmacokinetic or pharmacodynamic parameters. For some agents, equivalent dosages are determined empirically from the dose achieved to reach the same endpoint in an animal model or a clinical trial.

Peptide agents, such as Tat-NR2B9c are preferably delivered by infusion into a blood vessel, more preferably by intravenous infusion. The time of the infusion can affect both side effects (due e.g., to mast cell degranulation and histamine release) and efficacy. In general, for a given dosage level, a shorter infusion time is more likely to lead to histamine release. However, a shorter infusion time also may result in improved efficacy. Although practice of the invention is not dependent on an understanding of mechanism, the latter result can be explained both because of the delay being significant relative to development of pathology in the patient and because of the delay being significant relative to the plasma half life of the chimeric agent, as a result of which the chimeric agent does not reach an optimal therapeutic level. For the chimeric agent Tat-NR2B9c, a preferred infusion time providing a balance between these considerations is 5-15 minutes and more preferably 10 min. Indicated times should be understand as including a marking of error of +/−10%. Infusion times do not include any extra time for a wash out diffusion to wash out any remaining droplets from an initial diffusion that has otherwise proceeded to completion. The infusion times for Tat-NR2B9c can also serve as a guide for other pharmacological agents, optionally linked to internalization peptides, particularly close variants of Tat-NR2B9c, as discussed above.

VII. Pharmaceutical Compositions

The chimeric or other agents of the invention can be administered in the form of a pharmaceutical composition. Pharmaceutical compositions are typically manufactured under GMP conditions. Pharmaceutical compositions for parenteral administration are preferentially sterile (e.g., filter sterilization of peptide) and free of pyrogens. Pharmaceutical compositions can be provided in unit dosage form (i.e., the dosage for a single administration). Pharmaceutical compositions can be formulated in conventional manner using one or more physiologically acceptable carriers, diluents, excipients or auxiliaries that facilitate processing of chimeric agents into preparations which can be used pharmaceutically. Proper formulation is dependent on the route of administration chosen.

An exemplary formulation of the chimeric agent Tat-NR2B9c contains the peptide in normal saline (0.8-1.0% and preferably 0.9% saline) at a concentration of 10-30 mg/ml, for example 18-20 mg/ml. When stored frozen, such a composition is stable (insignificant degradation or aggregation of the peptide) for a period of two or more years. Although additional excipients can be added, nolinal saline without such excipients is sufficient to obtain this stability. For use such a composition is thawed and diluted into a larger volume of normal saline for infusion into a blood vessel. Another composition can be made by lyophilizing the chimeric agent Tat-NR2B9c at a concentration of 1-50 mg/ml in normal saline in the presence or absence of excipients. Such excipients can include those to increase stability or inhibit bacterial, viral or other pathogen growth that could degrade the drug. The lyophilized composition is stable at −20° C. or at room temperature. The lyophilized composition can be reconstituted in normal saline.

EXAMPLES

Example 1

Primate Model of Ischemic Stroke

The following example was performed on ten macaques divided into five test subjects and five controls. Each animal was put through the protocol twice with test animals in the first round serving as controls in the second round and vice versa.

Twenty 100-micron polystyrene spheres were delivered into an intracerebral vessel of each animal to induce embolic stroke. One hour after introducing the sphere, the animals were treated with Tat-NR2B9c (2.6 mg/kg) or vehicle control. The animals were then subject to MRI brain analysis and neurological examination at 4 hr, 24 hr and 14 days after introduction of the spheres.

After 14-28 days, the procedure was repeated with test animals serving as controls and vice versa.

FIG. 1 shows the MRI scan of infarctions 24 hr post injection of spheres in a control animal compared with a human having received endovascular surgery to insert a coil to repair an aneurysm. The number, size and appearance of infarctions relative to brain size are comparable between the human and the animal.

Figure 2:
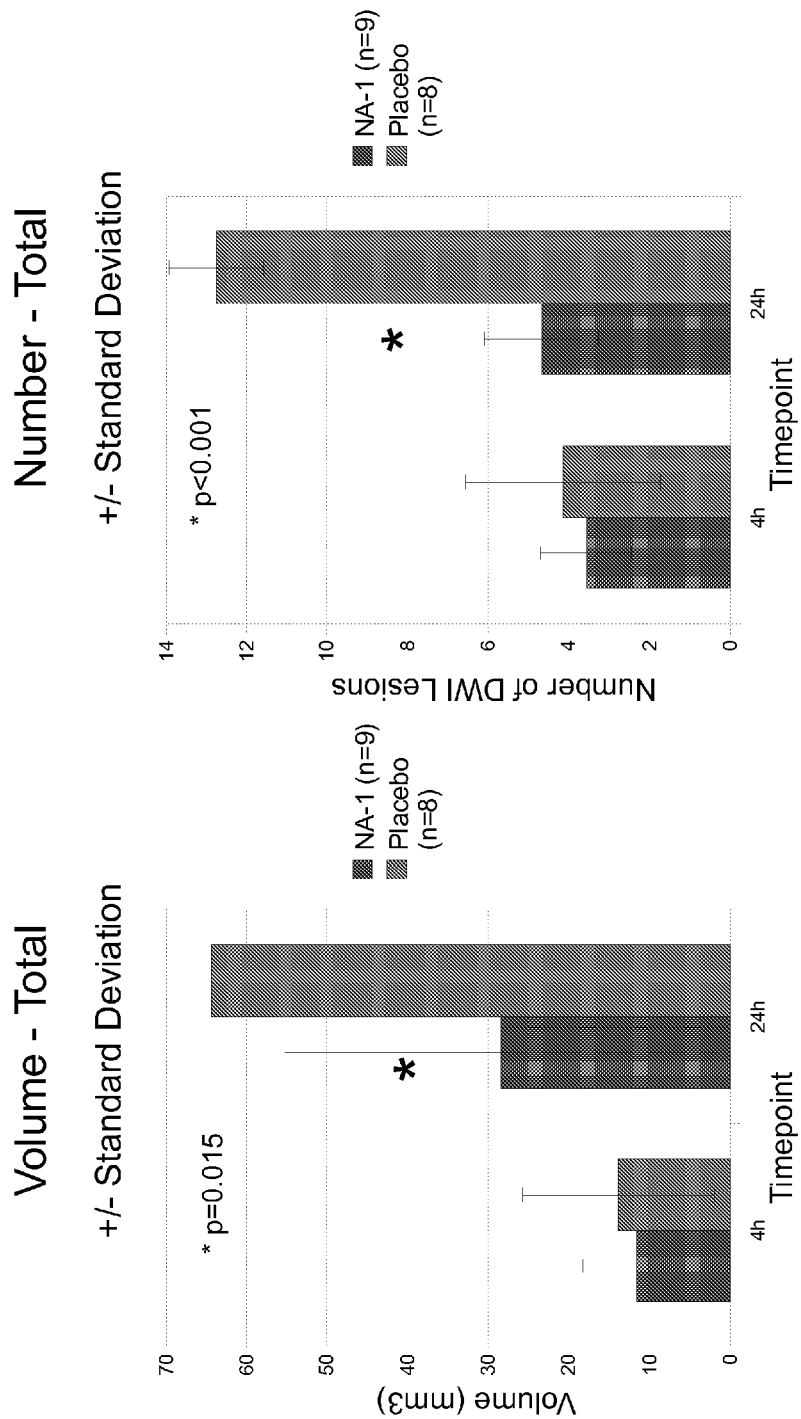
FIG. 2 compares the number and volume of MRI-visible infarctions in treated and control animals.
Figure 3:
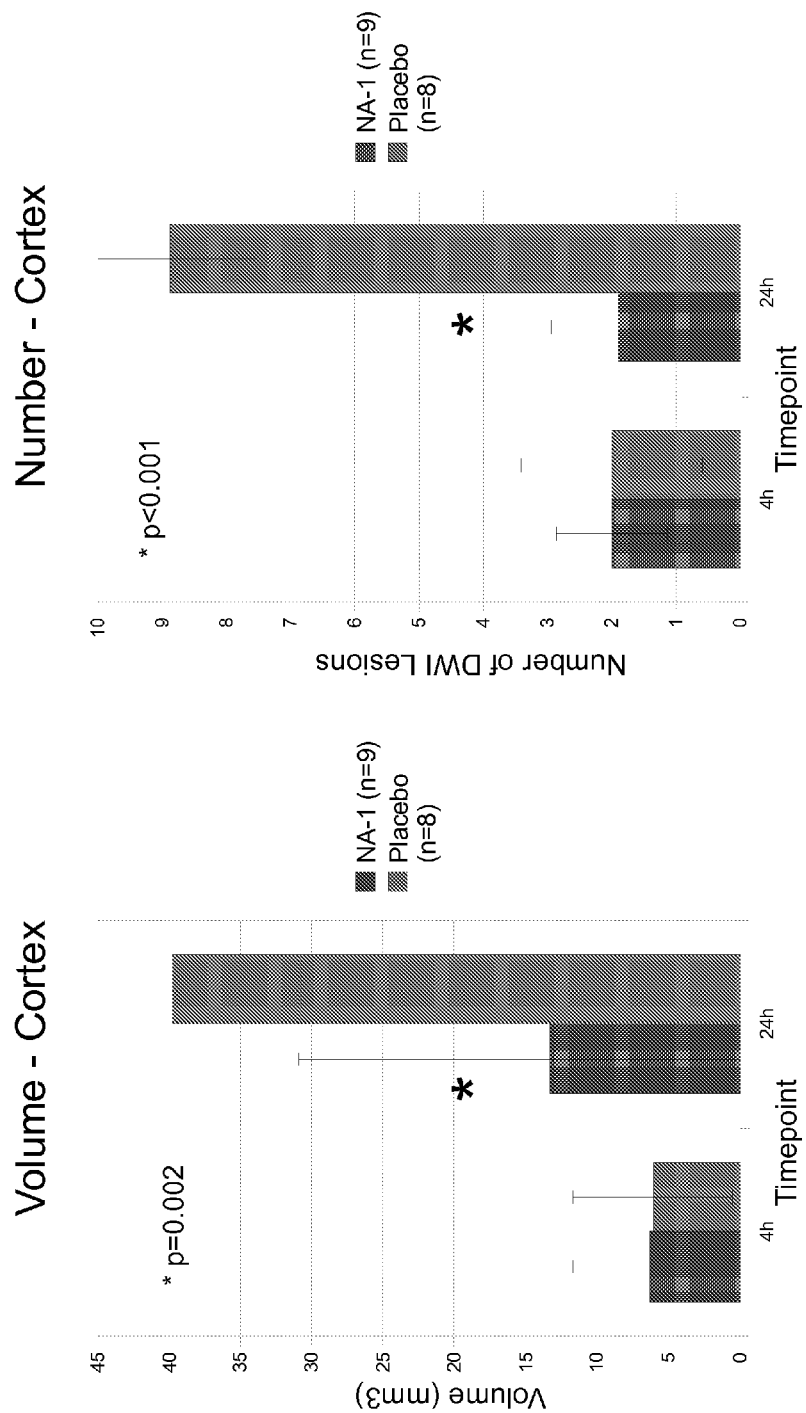
FIG. 3 shows similar data to FIG. 2 for infarctions in the cortex.

FIG. 2 compares the number and volume of MRI-visible infarctions in treated and control animals. Treatment with Tat-NR2B9c significantly reduced the number and volume of infarctions in the whole brain. FIG. 3 shows similar data for infarctions in the cortex. The reduction of number and volumes of infarctions was even greater in the cortex that the whole brain. Reduction in the cortex is particularly important because this region of the brain is primarily responsible for cognitive functioning.

Example 2

Infusion Time

Figure 4:
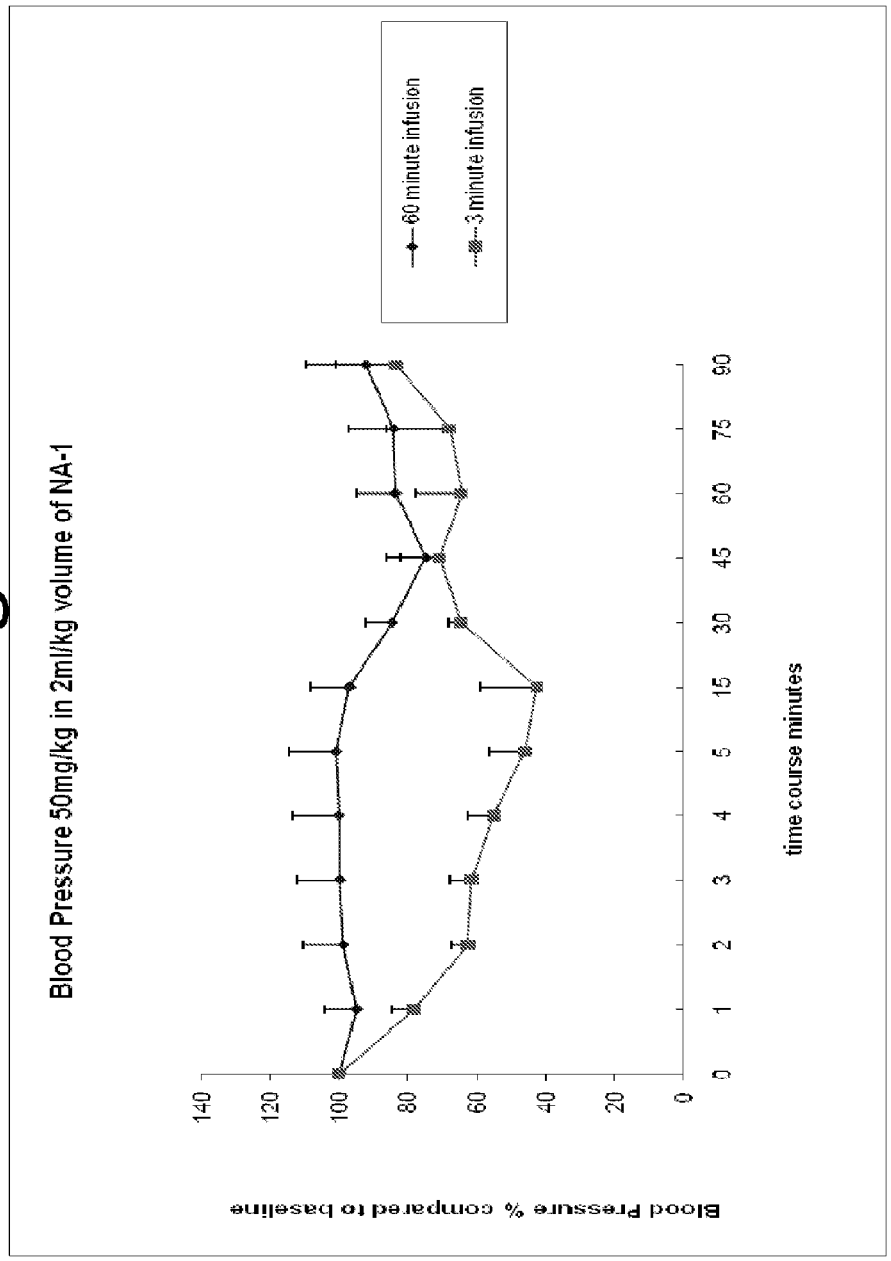
FIG. 4 shows changes in blood pressure following administration of Tat-NR2B9c at 50 mg/kg and an infusion time of 3 min or 60 min.

Tat-NR2B9c was administered to rats at 50 mg/kg and infusion times of 3 min or 60 min. FIG. 4 shows changes in blood pressure following administration. In rats infused over 3 min, the blood pressure decreased by about 50% before recovering over a period of 90 min. For rats infused over an hour there was only a slight reduction in blood pressure, which also recovered over a period of hour.

Figure 5:
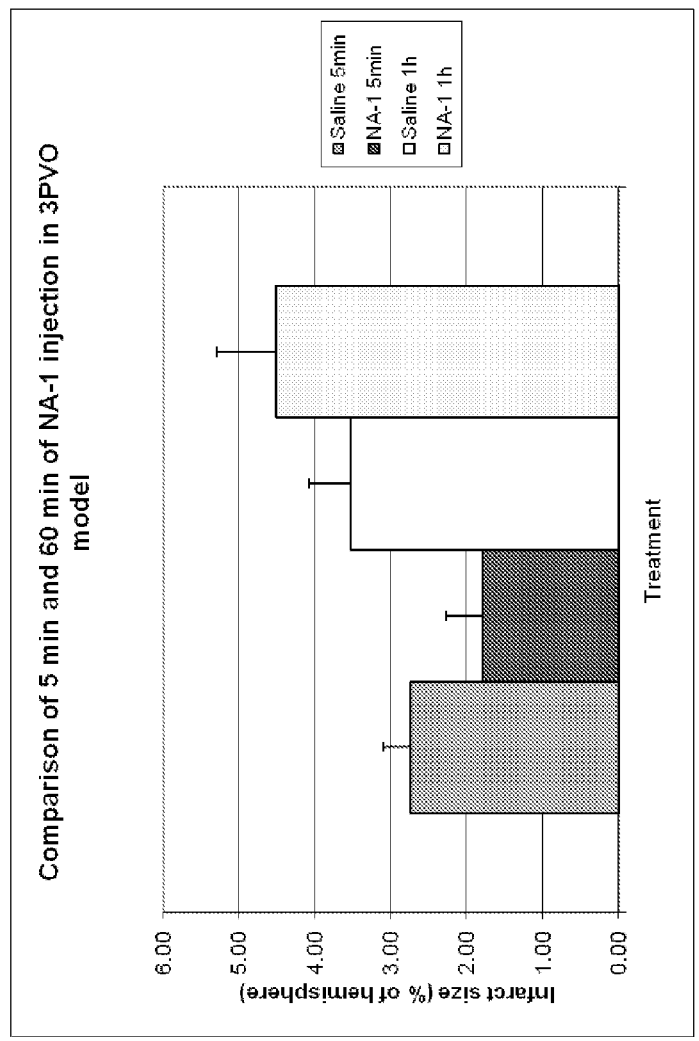
FIG. 5 shows infarction size measured 24 hr post treatment was significantly reduced relative to saline placebo with the 5 min infusion but not with the one hour infusion of Tat-NR 2B9c at 7.6 mg/kg (rightmost column).

Different infusion times were also compared for efficacy in a rat model of stroke in which adult Sprague Dawley rats (10-12 weeks old) (males~300 g, females~250 g) were fasted for 12-18 hours before being subjected to permanent pial vessel occlusion of 3 terminal branches of the Middle Cerebral Artery over the Whisker Barrel Cortex (P3VO). The protocol for analysis of this rat model has been described in WO/2008/008348. Tat-NR2B9c was administered at 7.6 mg/kg i.v. after vessel occlusion in comparison with vehicle. Two periods of infusion were compared, 5 min and 1 hour. FIG. 5 shows infarction size measured 24 hr post treatment was significantly reduced relative to saline placebo with the 5 min infusion but not with the one hour infusion.

Example 3

Phase I Clinical Trial

We carried out a Safety, Tolerability and Pharmacokinetic Study of Tat-NR2B9c in humans. Subjects were either normal, healthy, non-smoking males or post-menopausal or surgically sterile female subjects with a minimum age of 18 years. The subjects were either administered Tat-NR2B9c, Lot #: 124-134-001B, or were given placebo (Phosphate Buffered Saline), Lot #: 124-134-001A, administered as an intravenous infusion (10±1 minutes). Four subjects were dosed in each of Cohorts 1 to 3, and 10 subjects were dosed in each of Cohorts 4 to 8. All 62 subjects completed the study.

Methods

Blood Draw Timepoints:

During the study period, 11 blood samples were collected for pharmacokinetic analysis from each subject at the following timepoints: 0.00 (pre-dose), 0.08 (5 minutes), 0.17 to 0.25 (10 to 15 minutes, precisely at the end of each individual drug infusion), 0.33 (20 minutes), 0.50, 0.75, 1.00, 2.00, 6.00, 12.00, and 24.00 hours post-dose. In addition, 8 blood samples were collected for histamine analysis from each subject at the following timepoints: 0.00 (pre-dose), and at 0.08 (5 minutes), 0.17 (10 minutes), 0.25, 0.50, 1.00, 2.00, and 24.00 hours post-dose.

Safety Assessment:

The safety assessment was performed on all subjects who received at least 1 dose during the course of the study. The incidents of all adverse events (AEs) were tabulated by treatment and subject number. Absolute values for vital signs, electrocardiogram (ECG) parameters, laboratory parameters and physical examinations were also documented and values outside the normal range were flagged. Shifts from baseline values were tabulated. AEs were documented using investigator and Medical Dictionary for Regulatory Activities (MedDRA) terms.

A. Results

Seven of 8 subjects in the 3.75 mg/kg dose group had histamine levels greater than 10 nmol/L (average 24.3 nmol/L; maximum of 39.8 nmol/L) 10 minutes after the start of NA 1 administration, and 3 of the subjects still had histamine levels greater than 10 nmol/L (average 15.3 nmol/L; maximum of 20.3 nmol/L) 15 minutes after the start of NA 1 administration.

Other than the 3.75 mg/kg dose group, no treatment group had significant abnormal levels of histamine. The placebo group and the 0.375 mg/kg dose group each had 1 subject that had an elevated histamine level at 1 timepoint, but these results were at screening and at 2.00 hours post dose, respectively. All abnormal histamine results returned to the normal range within 24.00 hours of drug administration.

Forty subjects who participated in the study experienced a total of 168 adverse effects (AEs) during the study. The majority of AEs were mild in severity. Thirty-four of 46 active treatment subjects (73.9%) experienced at least 1 AE, while 6 of 16 placebo treatment subjects (37.5%) experienced at least 1 AE. Subjects in the 2.60 and 3.75 mg/kg dose groups experienced significantly more AEs than subjects in the lower dose groups. No Serious Adverse Events (SAEs) were reported. The most common AEs experienced by subjects receiving Tat-NR2B9c were feeling hot (13/46; 28.3%), pruritis (12/46; 26.1%), flushing (10/46; 21.7%), and dry mouth (9/46; 19.6%). All AEs were resolved with the exception of 2 instances of increased blood glucose, as the subjects were lost to follow-up.

The incidence of AEs in the 2.60 and 3.75 mg/kg dose groups was higher than the AE incidence rate in the placebo, 0.02, 0.08, 0.20, 0.375, 0.75 and 1.50 mg/kg dose groups. At doses of Tat-NR2B9c≥2.60 mg/kg, several AEs were frequently reported. These included: (1) decreases in blood pressure, (2) tingling sensation (paraesthesia), (3) numbness (hypoaesthesia), (4) redness (erythema), (5) rash, (6) itchiness (pruritus), (7) dry mouth, (8) nausea, (9) feeling hot, and (10) flushing. The onset of these AEs coincided with the administration of the study drug and was probably related to the study drug.

In preclinical trials on rats, dogs and primates, with Tat-NR2B9c, elevated histamine levels were observed in high dose groups, and were likely the source of side effects including swelling, redness and hypotension. In the current study, histamine levels were elevated in 7 of the 8 subjects in the highest dose group (3.75 mg/kg) 10 minutes after the start of the intravenous drug administration, and remained elevated in 3 of these subjects 15 minutes after drug administration, after which time levels returned to the normal range. During the same time frame that histamine levels were elevated, most of the AEs in the 3.75 mg/kg dose group were observed. This suggests that the elevated histamine levels were the source of the most frequently reported AEs (including decreased blood pressure, tingling, numbness, redness, rash, itchiness, dry mouth, nausea, feeling hot, and flushing).

Example 4

Clinical Trial of Tat-NR2B9c in Patients Undergoing Neurointerventional Aneurysm Repair Procedures The primary measure of efficacy is the total volume of MRI-detectable DWI and FLAIR-sequence—positive lesions following endovascular intervention. If there are a number of patients with large volume stroke, these outlier volumes are truncated to a maximum of 10 cc to allow for a more nounal distribution of volumes and testing with standard parametric statistics. The primary analysis is a t-test, with a null hypothesis of equivalent means in the two treatment groups (drug vs. Placebo) and an alternative hypothesis that the mean lesion total volume in the treatment group is smaller than the placebo group. The maximum sample size of the trial is 400, with 200 per treatment arm.

A determination of the efficacy of a single intravenous dose of agent in reducing the number of embolic strokes induced by the endovascular treatment is based on counts of strokes from the DWI/FLAIR MRI sequences. The number of strokes per patient in each of the treated and placebo groups is sorted into five categories as follows: 0 (no strokes), 1, 2, 3, and 4 or more strokes.

The ability of the agent to reduce procedurally-induced vascular cognitive impairment is determined using a weighted composite score obtained from the neurocognitive test Battery.

To determine the efficacy of the agent in reducing the frequency of large (>10 cc volume) strokes, the number of large strokes in the treated and placebo group is compared using a contingency table analysis as above.

Modified Rankin Scores (mRS; range, 0 to 5, with 0 indicating no residual symptoms and 5 indicating bedbound, requiring constant care) in patients undergoing the endovascular procedure are dichotomized into mRS 0 to 2 (indicating independent functioning) and mRS of 3 or greater, indicating death or dependency. The NIH stroke scale (NIHSS; scores range from 0 to 42, with higher scores indicating increasing severity) data are assessed as a dichotomy: NIHSS 0-1 vs. 2 or greater using a Chi-square or Fisher's exact test. The analysis is further stratified according to whether or not the patient presented with a subarachnoid hemorrhage.

Dosing begins as soon as the endovascular repair of the brain aneurysm has been completed (typically after insertion of the final coil or stent) and the final angiographic imaging has been completed. Dose timing starts at the time of drip onset. Dosing is performed by administering the contents of the 100 mL bag to the subject through an intravenous catheter inserted into a vein in the upper extremity and using an infusion pump [e.g., FLO-GARD Volumetric Infusion Pump 6201 or equivalent]. Dosing is carried out evenly over the course of 10±1 minutes while the IV bag contents are administered to the subject. The entire volume (treatment dose) of the IV mini-bag is administered. After the dose administration, a minimum of 10 mL (not to exceed 15 mL) of saline is administered using the infusion pump to flush any remaining medication left within the IV tubing.

Example 5

Dose Preparation

Syringe vials containing Tat-NR2B9c in normal (0.9%) saline or placebo are stored at the pharmacy of each clinical site at −20° C. On enrolment of a study subject, one or more (depending on the total required) Tat-NR2B9c drug or placebo syringe vial is elected at the pharmacy based upon a drug:placebo randomization code and thawed before use. A syringe for each individual subject dosing is labeled with the subject number and prepared by calculating the volume to draw from the syringe vial as follows: (2.60 mg/kg× subject weight in kg)/[Drug Potency in mg/ml]. This determines the number of milliliters to pull up into the syringe. The syringe containing Tat-NR2B9c or placebo is delivered to the dosing site and there injected into the IV port of a 100 mL drip bag of 0.9% normal saline.

Although the invention has been described in detail for purposes of clarity of understanding, it will be obvious that certain modifications may be practiced within the scope of the appended claims. All publications, accession numbers, and patent documents cited in this application are hereby incorporated by reference in their entirety for all purposes to the same extent as if each were so individually denoted. To the extent more than one sequence is associated with an accession number at different times, the sequences associated with the accession number as of the effective filing date of this application is meant. The effective filing date is the date of the earliest priority application disclosing the accession number in question. Unless otherwise apparent from the context any element, embodiment, step, feature or aspect of the invention can be performed in combination with any other.

What is claimed is:

1. A method of inhibiting ischemic damage from endovascular surgery to treat an aneurysm, diagnostic angiography or carotid stenting in a subject comprising administering an effective regime of an agent that inhibits binding of PSD-95 to NMDAR 2B to the subject thereby inhibiting neurological behavioral impairment agent, wherein the agent comprises a peptide with a C-terminal sequence of ESDV (SEQ ID NO:12) or ETDV (SEQ ID NO:39) linked to an internationalization peptide.

2. The method of claim 1, wherein ischemic damage is from diagnostic angiography of the brain.

3. The method of claim 1, wherein ischemic damage is from endovascular surgery to treat an aneurysm.

4. The method of claim 1, wherein the agent is administered before the endovascular surgery.

5. The method of claim 1, wherein the agent is administered within 1 hour of completing endovascular surgery.

6. The method of claim 1, wherein the endovascular surgery comprises inserting a coil into the aneurysm.

7. The method of claim 1, wherein the endovascular surgery comprises inserting a stent into the vessel subject to the aneurysm.

8. The method of claim 1, wherein the endovascular surgery comprises inserting a microcatheter.

9. The method of claim 5, wherein the agent is administered as a single-dose regime.

10. The method of claim 1, wherein the dose is 2-3 mg/kg.

11. The method of claim 1, wherein the agent is Tat-NR2B9c.

12. The method of claim 1, wherein the agent is administered with a mast cell degranulation inhibitor or an antihistamine.

* * * * *

SEQUENCE LISTING

```
<160> NUMBER OF SEQ ID NOS: 72

<210> SEQ ID NO 1
<211> LENGTH: 10
<212> TYPE: PRT
<213> ORGANISM: Artificial Sequence
<220> FEATURE:
```

```
<223> OTHER INFORMATION: Synthetic tat peptide

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 2

Tyr Gly Arg Lys Lys Arg Arg Gln Arg Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 3

Phe Gly Arg Lys Lys Arg Arg Gln Arg Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic tat peptide

<400> SEQUENCE: 4

Gly Arg Lys Lys Arg Arg Gln Arg Arg Arg Pro Gln
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic pharmacologic agent

<400> SEQUENCE: 5

Lys Leu Ser Ser Ile Glu Ser Asp Val
1               5

<210> SEQ ID NO 6
<211> LENGTH: 20
<212> TYPE: PRT
<213> ORGANISM: Artificial Sequence
<220> FEATURE:
<223> OTHER INFORMATION: Synthetic Tat-NR2B9c peptide

<400> SEQUENCE: 6

Tyr Gly Arg Lys Lys Arg Arg Gln Arg Arg Arg Lys Leu Ser Ser Ile
1               5                   10                  15

Glu Ser Asp Val
            20

<210> SEQ ID NO 7
<211> LENGTH: 20
<212> TYPE: PRT
```

<213> ORGANISM: Artificial Sequence
<220> FEATURE:
<223> OTHER INFORMATION: Synthetic Tat-NR2B9c peptide with 2 point
      mutations in the PSD-95 binding domain

<400> SEQUENCE: 7

Tyr Gly Arg Lys Lys Arg Arg Gln Arg Arg Lys Leu Ser Ser Ile
1               5                   10                  15

Glu Ala Asp Ala
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic F-Tat-NR2B9c peptide

<400> SEQUENCE: 8

Phe Gly Arg Lys Lys Arg Arg Gln Arg Arg Lys Leu Ser Ser Ile
1               5                   10                  15

Glu Ser Asp Val
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic Tat-NR2B9c K>A peptide

<400> SEQUENCE: 9

Tyr Gly Arg Lys Lys Arg Arg Gln Arg Arg Ala Leu Ser Ser Ile
1               5                   10                  15

Glu Ser Asp Val
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic F-Tat-NR2B9c K>A peptide

<400> SEQUENCE: 10

Phe Gly Arg Lys Lys Arg Arg Gln Arg Arg Ala Leu Ser Ser Ile
1               5                   10                  15

Glu Ser Asp Val
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      NMDAR2B

<400> SEQUENCE: 11

Phe Asn Gly Ser Ser Asn Gly His Val Tyr Glu Lys Leu Ser Ser Ile
1               5                   10                  15

Glu Ser Asp Val
            20

```
<210> SEQ ID NO 12
<211> LENGTH: 4
<212> TYPE: PRT
<213> ORGANISM: Artificial Sequence
<220> FEATURE:
<223> OTHER INFORMATION: Synthetic  PL motif of NMDAR2B

<400> SEQUENCE: 12

Glu Ser Asp Val
1

<210> SEQ ID NO 13
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      NMDAR1, NMDAR1-1, NMDAR1-4, NMDAR1-3b, NMDAR1-4b

<400> SEQUENCE: 13

His Pro Thr Asp Ile Thr Gly Pro Leu Asn Leu Ser Asp Pro Ser Val
1               5                   10                  15

Ser Thr Val Val
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      NMDAR1-2, NMDAR1-3

<400> SEQUENCE: 14

Arg Arg Ala Ile Glu Arg Glu Glu Gly Gln Leu Gln Leu Cys Ser Arg
1               5                   10                  15

His Arg Glu Ser
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      NMDAR2C

<400> SEQUENCE: 15

Thr Gln Gly Phe Pro Gly Pro Cys Thr Trp Arg Arg Ile Ser Ser Leu
1               5                   10                  15

Glu Ser Glu Val
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      NMDAR3A

<400> SEQUENCE: 16

Ala Val Ser Arg Lys Thr Glu Leu Glu Glu Tyr Gln Arg Thr Ser Arg
1               5                   10                  15

Thr Cys Glu Ser
            20
```

```
<210> SEQ ID NO 17
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      NMDAR2

<400> SEQUENCE: 17

Leu Asn Ser Cys Ser Asn Arg Arg Val Tyr Lys Lys Met Pro Ser Ile
1               5                   10                  15

Glu Ser Asp Val
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      NMDAR2D

<400> SEQUENCE: 18

Gly Gly Asp Leu Gly Thr Arg Arg Gly Ser Ala His Phe Ser Ser Leu
1               5                   10                  15

Glu Ser Glu Val
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      glutamate receptor delta 2

<400> SEQUENCE: 19

Gln Pro Thr Pro Thr Leu Gly Leu Asn Leu Gly Asn Asp Pro Asp Arg
1               5                   10                  15

Gly Thr Ser Ile
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      glutamate receptor 1

<400> SEQUENCE: 20

Met Gln Ser Ile Pro Cys Met Ser His Ser Ser Gly Met Pro Leu Gly
1               5                   10                  15

Ala Thr Gly Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      glutamate receptor 2

<400> SEQUENCE: 21
```

```
Gln Asn Phe Ala Thr Tyr Lys Glu Gly Tyr Asn Val Tyr Gly Ile Glu
1               5                   10                  15

Ser Val Lys Ile
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      glutamate receptor 3

<400> SEQUENCE: 22

Gln Asn Tyr Ala Thr Tyr Arg Glu Gly Tyr Asn Val Tyr Gly Thr Glu
1               5                   10                  15

Ser Val Lys Ile
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      glutamate receptor 4

<400> SEQUENCE: 23

His Thr Gly Thr Ala Ile Arg Gln Ser Ser Gly Leu Ala Val Ile Ala
1               5                   10                  15

Ser Asp Leu Pro
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      glutamate receptor 5

<400> SEQUENCE: 24

Ser Phe Thr Ser Ile Leu Thr Cys His Gln Arg Arg Thr Gln Arg Lys
1               5                   10                  15

Glu Thr Val Ala
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic  C-terminal 20-mer sequence of
      glutamate receptor 6

<400> SEQUENCE: 25

Glu Val Ile Asn Met His Thr Phe Asn Asp Arg Arg Leu Pro Gly Lys
1               5                   10                  15

Glu Thr Met Ala
            20

<210> SEQ ID NO 26
<211> LENGTH: 20
<212> TYPE: PRT
```

-continued

<213> ORGANISM: Artificial Sequence
<220> FEATURE:
<223> OTHER INFORMATION: Synthetic C-terminal 20-mer sequence of
      glutamate receptor 7

<400> SEQUENCE: 26

Arg Arg Leu Pro Gly Lys Asp Ser Met Ala Cys Ser Thr Ser Leu Ala
1               5                   10                  15

Pro Val Phe Pro
            20

<210> SEQ ID NO 27
<211> LENGTH: 4
<212> TYPE: PRT
<213> ORGANISM: Artificial Sequence
<220> FEATURE:
<223> OTHER INFORMATION: Synthetic C-terminal 4-mer sequence of
      NMDAR1, NMDAR1-1, NMDAR1-4, NMDAR1-3b, NMDAR1-4b

<400> SEQUENCE: 27

Ser Thr Val Val
1

<210> SEQ ID NO 28
<211> LENGTH: 4
<212> TYPE: PRT
<213> ORGANISM: Artificial Sequence
<220> FEATURE:
<223> OTHER INFORMATION: Synthetic C-terminal 4-mer sequence of
      NMDAR1-2, NMDAR1-3

<400> SEQUENCE: 28

His Arg Glu Ser
1

<210> SEQ ID NO 29
<211> LENGTH: 4
<212> TYPE: PRT
<213> ORGANISM: Artificial Sequence
<220> FEATURE:
<223> OTHER INFORMATION: Synthetic C-terminal 4-mer sequence of
      NMDAR2C, NMDAR2D

<400> SEQUENCE: 29

Glu Ser Glu Val
1

<210> SEQ ID NO 30
<211> LENGTH: 4
<212> TYPE: PRT
<213> ORGANISM: Artificial Sequence
<220> FEATURE:
<223> OTHER INFORMATION: Synthetic C-terminal 4-mer sequence of
      NMDAR3A

<400> SEQUENCE: 30

Thr Cys Glu Ser
1

<210> SEQ ID NO 31
<211> LENGTH: 4
<212> TYPE: PRT
<213> ORGANISM: Artificial Sequence
<220> FEATURE:
<223> OTHER INFORMATION: Synthetic C-terminal 4-mer sequence of
      glutamate receptor delta 2

<400> SEQUENCE: 31

Gly Thr Ser Ile
1

<210> SEQ ID NO 32
<211> LENGTH: 4
<212> TYPE: PRT
<213> ORGANISM: Artificial Sequence
<220> FEATURE:
<223> OTHER INFORMATION: Synthetic  C-terminal 4-mer sequence of
      glutamate receptor 1

<400> SEQUENCE: 32

Ala Thr Gly Leu
1

<210> SEQ ID NO 33
<211> LENGTH: 4
<212> TYPE: PRT
<213> ORGANISM: Artificial Sequence
<220> FEATURE:
<223> OTHER INFORMATION: Synthetic  C-terminal 4-mer sequence of
      glutamate receptor 2 and glutamate receptor 3

<400> SEQUENCE: 33

Ser Val Lys Ile
1

<210> SEQ ID NO 34
<211> LENGTH: 4
<212> TYPE: PRT
<213> ORGANISM: Artificial Sequence
<220> FEATURE:
<223> OTHER INFORMATION: Synthetic  C-terminal 4-mer sequence of
      glutamate receptor 4

<400> SEQUENCE: 34

Ser Asp Leu Pro
1

<210> SEQ ID NO 35
<211> LENGTH: 4
<212> TYPE: PRT
<213> ORGANISM: Artificial Sequence
<220> FEATURE:
<223> OTHER INFORMATION: Synthetic  C-terminal 4-mer sequence of
      glutamate receptor 5

<400> SEQUENCE: 35

Glu Thr Val Ala
1

<210> SEQ ID NO 36
<211> LENGTH: 4
<212> TYPE: PRT
<213> ORGANISM: Artificial Sequence
<220> FEATURE:
<223> OTHER INFORMATION: Synthetic  C-terminal 4-mer sequence of
      glutamate receptor 6

<400> SEQUENCE: 36

Glu Thr Met Ala
1

<210> SEQ ID NO 37
<211> LENGTH: 4
<212> TYPE: PRT
<213> ORGANISM: Artificial Sequence

```
<220> FEATURE:
<223> OTHER INFORMATION: Synthetic  C-terminal 4-mer sequence of
      glutamate receptor 7

<400> SEQUENCE: 37

Pro Val Phe Pro
1

<210> SEQ ID NO 38
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = Glu, Asp, Asn or Gln
<220> FEATURE:
<221> NAME/KEY: MOD_RES
<222> LOCATION: (2)..(2)
<223> OTHER INFORMATION: Xaa = Ser or Thr
<220> FEATURE:
<221> NAME/KEY: MOD_RES
<222> LOCATION: (3)..(3)
<223> OTHER INFORMATION: Xaa = Asp, Glu, Gln or Asn
<220> FEATURE:
<221> NAME/KEY: MOD_RES
<222> LOCATION: (4)..(4)
<223> OTHER INFORMATION: Xaa = Val or Leu

<400> SEQUENCE: 38

Xaa Xaa Xaa Xaa
1

<210> SEQ ID NO 39
<211> LENGTH: 4
<212> TYPE: PRT
<213> ORGANISM: Artificial Sequence
<220> FEATURE:
<223> OTHER INFORMATION: Synthetic peptide

<400> SEQUENCE: 39

Glu Thr Asp Val
1

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide

<400> SEQUENCE: 40

Glu Thr Glu Val
1

<210> SEQ ID NO 41
<211> LENGTH: 4
<212> TYPE: PRT
<213> ORGANISM: Artificial Sequence
<220> FEATURE:
<223> OTHER INFORMATION: Synthetic peptide

<400> SEQUENCE: 41

Asp Thr Asp Val
1

<210> SEQ ID NO 42
```

```
<211> LENGTH: 4
<212> TYPE: PRT
<213> ORGANISM: Artificial Sequence
<220> FEATURE:
<223> OTHER INFORMATION: Synthetic peptide

<400> SEQUENCE: 42

Asp Thr Glu Val
1

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Lys Leu Ser Ser Ile Glu Thr Asp Val
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Gly Ser Ser Ser Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

Thr Gly Glu Lys Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide

<400> SEQUENCE: 46

Gly Gly Arg Arg Gly Gly Gly Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Leu Arg Gln Arg Asp Gly Glu Arg Pro
1               5

<210> SEQ ID NO 48
<211> LENGTH: 13
```

```
<212> TYPE: PRT
<213> ORGANISM: Artificial Sequence
<220> FEATURE:
<223> OTHER INFORMATION: Synthetic peptide

<400> SEQUENCE: 48

Tyr Gly Arg Lys Lys Arg Arg Gln Arg Arg Pro Gln
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic variant of tat peptide
<220> FEATURE:
<221> NAME/KEY: MOD_RES
<222> LOCATION: (1)..(1)
<223> OTHER INFORMATION: Xaa is any amino acid other than Tyr or absent

<400> SEQUENCE: 49

Xaa Gly Arg Lys Lys Arg Arg Gln Arg Arg Arg
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 50

Gly Lys Lys Lys Lys Lys Gln Lys Lys Lys
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 51

Arg Lys Lys Arg Arg Gln Arg Arg Arg
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 52

Gly Ala Lys Lys Arg Arg Gln Arg Arg Arg
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 53

Ala Lys Lys Arg Arg Gln Arg Arg Arg
1               5
```

<210> SEQ ID NO 54
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 54

Gly Arg Lys Ala Arg Arg Gln Arg Arg Arg
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 55

Arg Lys Ala Arg Arg Gln Arg Arg Arg
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 56

Gly Arg Lys Lys Ala Arg Gln Arg Arg Arg
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 57

Arg Lys Lys Ala Arg Gln Arg Arg Arg
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 58

Gly Arg Lys Lys Arg Arg Gln Ala Arg Arg
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 59

Arg Lys Lys Arg Arg Gln Ala Arg Arg
1               5

```
<210> SEQ ID NO 60
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 60

Gly Arg Lys Lys Arg Arg Gln Arg Ala Arg
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 61

Arg Lys Lys Arg Arg Gln Arg Ala Arg
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 62

Arg Arg Pro Arg Arg Pro Arg Arg Pro Arg Arg
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 63

Arg Arg Ala Arg Arg Ala Arg Arg Ala Arg Arg
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 64

Arg Arg Arg Ala Arg Arg Arg Ala Arg Arg
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 65

Arg Arg Arg Pro Arg Arg Arg Pro Arg Arg
1               5                   10

<210> SEQ ID NO 66
```

```
<211> LENGTH: 8
<212> TYPE: PRT
<213> ORGANISM: Artificial Sequence
<220> FEATURE:
<223> OTHER INFORMATION: Synthetic tat peptide

<400> SEQUENCE: 66

Arg Arg Pro Arg Arg Pro Arg Arg
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic tat peptide

<400> SEQUENCE: 67

Arg Arg Ala Arg Arg Ala Arg Arg
1               5

<210> SEQ ID NO 68
<211> LENGTH: 4
<212> TYPE: PRT
<213> ORGANISM: Artificial Sequence
<220> FEATURE:
<223> OTHER INFORMATION: synthetic peptide analog of NR2B9c
<220> FEATURE:
<221> NAME/KEY: MOD_RES
<222> LOCATION: (1)...(1)
<223> OTHER INFORMATION: Xaa = Glu, Gln, and Ala, or an analogue
      thereof
<220> FEATURE:
<221> NAME/KEY: MOD_RES
<222> LOCATION: (2)...(2)
<223> OTHER INFORMATION: Xaa = Thr or Ser
<220> FEATURE:
<221> NAME/KEY: MOD_RES
<222> LOCATION: (3)...(3)
<223> OTHER INFORMATION: Xaa = Ala, Gln, Asp, Asn, N-Me-Ala, N-Me-Gln,
      N-Me-Asp,and N-Me-Asn or an analogue thereof

<400> SEQUENCE: 68

Xaa Xaa Xaa Val
1

<210> SEQ ID NO 69
<211> LENGTH: 22
<212> TYPE: PRT
<213> ORGANISM: Artificial Sequence
<220> FEATURE:
<223> OTHER INFORMATION: synthetic retro-inverso analog of Tat-NR2B9c

<400> SEQUENCE: 69

Val Asp Ser Glu Ile Ser Ser Leu Lys Arg Arg Arg Gln Arg Arg Lys
1               5                   10                  15

Lys Arg Gly Tyr Ile Asn
            20

<210> SEQ ID NO 70
<211> LENGTH: 20
<212> TYPE: PRT
<213> ORGANISM: Artificial Sequence
<220> FEATURE:
<223> OTHER INFORMATION: synthetic peptide RvTat-NR2B9c

<400> SEQUENCE: 70

Arg Arg Arg Gln Arg Arg Lys Lys Arg Gly Tyr Lys Leu Ser Ser Ile
1               5                   10                  15
```

```
Glu Ser Asp Val
        20

<210> SEQ ID NO 71
<211> LENGTH: 5
<212> TYPE: PRT
<213> ORGANISM: Artificial Sequence
<220> FEATURE:
<223> OTHER INFORMATION: synthetic pentamer peptide from the C-terminus
      of NMDAR 2B

<400> SEQUENCE: 71

Ile Glu Ser Asp Val
1               5

<210> SEQ ID NO 72
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 72

Gly Arg Lys Lys Arg Arg Gln Arg Arg Arg Pro
1               5                   10
```